(12) United States Patent
Nihira et al.

(10) Patent No.: US 9,814,776 B2
(45) Date of Patent: Nov. 14, 2017

(54) PHARMACEUTICAL PREPARATION COMPRISING AMINOPYRAZOLE DERIVATIVE

(71) Applicant: Chugai Seiyaku Kabushiki Kaisha, Tokyo (JP)

(72) Inventors: Jun Nihira, Tokyo (JP); Kensuke Okazaki, Tokyo (JP); Shiho Yoshimura, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 132 days.

(21) Appl. No.: 14/430,273

(22) PCT Filed: Jul. 31, 2014

(86) PCT No.: PCT/JP2014/070154
§ 371 (c)(1),
(2) Date: Aug. 20, 2015

(87) PCT Pub. No.: WO2015/016295
PCT Pub. Date: Feb. 5, 2015

(65) Prior Publication Data
US 2015/0238607 A1    Aug. 27, 2015

(30) Foreign Application Priority Data
Jul. 31, 2013 (JP) .................. 2013-159521

(51) Int. Cl.
A61K 31/415    (2006.01)
C07C 305/00    (2006.01)
A61K 47/20    (2006.01)
A61K 31/4184    (2006.01)
A61K 9/20    (2006.01)

(52) U.S. Cl.
CPC ............ *A61K 47/20* (2013.01); *A61K 9/2018* (2013.01); *A61K 9/2054* (2013.01); *A61K 31/4184* (2013.01)

(58) Field of Classification Search
None
See application file for complete search history.

(56) References Cited

U.S. PATENT DOCUMENTS

| 8,829,199 B2 | 9/2014 | Taka et al. | |
| 2007/0287838 A1* | 12/2007 | Niculescu-Duvaz | C07D 471/04 546/118 |
| 2014/0315856 A1* | 10/2014 | Taka | A61K 31/4184 514/63 |

FOREIGN PATENT DOCUMENTS

| CN | 101084217 | 12/2007 |
| CN | 102574836 | 7/2012 |
| EP | 2 471 786 | 7/2012 |
| JP | S58-76475 | 5/1983 |
| JP | 2011-528686 | 11/2011 |
| JP | 2012-180344 | 9/2012 |
| WO | WO 2006/043090 | 4/2006 |
| WO | WO 2010/010017 | 1/2010 |
| WO | WO 2011/016528 | 2/2011 |
| WO | WO 2011016528 A1 * | 2/2011 ......... A61K 31/4184 |

OTHER PUBLICATIONS

Qiang et al. Drug Development and Industrial Pharmacy, 2010 (36) 1486-1496.*
Aljaberi et al. Pharmaceutical Development and Technology, 2013 (18) 490-503.*
Bolhuis et al. European Journal of Pharmaceutical Sciences, 1997 (5) 63-69.*
Mohanachandran et al. International Journal of Pharmaceutical Sciences Review and Research 2011 (6) 105-109.*
Stahl, Process Worldwide 2010, 34-39.*
Eswarakumar et al., "Cellular signaling by fibroblast growth factor receptors," *Cytokine Growth Factor Rev.*, Apr. 2005;16(2):139-49. Epub Feb. 1, 2005.
International Search Report for App. Ser. No. PCT/JP2014/070154, dated Sep. 16, 2014, 3 pages.
Kibbe, "Handbook of Pharmaceutical Excipients, Sodium Lauryl Sulfate," 487-489 (Jan. 1, 2000).
Kibbe, "Handbook of Pharmaceutical Excipients, Talc," 555-567 (Jan. 1, 2000).
European Search Report for App. Ser. No. EP 14 83 2164, dated Dec. 16, 2015, 7 pages.
International Preliminary Report on Patentability issued in PCT App. No. PCT/JP2014/070154, dated Feb. 2, 2016, 6 pages.
Li, "Guangdong Pharmaceutical", "Investigation on Factors Influencing Dissolution Degree of Tablets", vol. 15, No. 5, p. 19-21, Oct. 25, 2005 (with English translation).
Zhang, "Industrial Pharmaceutics", Ruhua Zhang, p. 335, China Medical Science Press, Sep. 1998 (with English translation).

* cited by examiner

*Primary Examiner* — Jeffrey S Lundgren
*Assistant Examiner* — Michael Schmitt
(74) *Attorney, Agent, or Firm* — Fish & Richardson P.C.

(57) ABSTRACT

The pharmaceutical formulations according to the present invention include an alkyl sulfate salt and a compound represented by general formula (I) below (where $R_1$ to $R_4$ are as defined in the specification) or tautomers thereof, or pharmaceutically acceptable salts thereof.

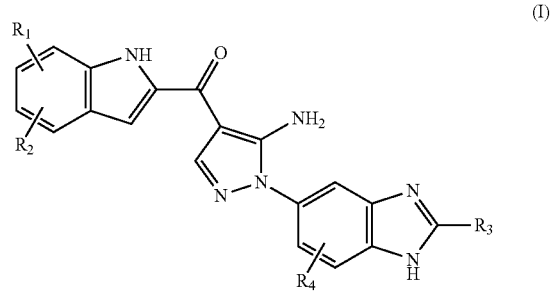

(I)

46 Claims, 3 Drawing Sheets

PHARMACEUTICAL PREPARATION COMPRISING AMINOPYRAZOLE DERIVATIVE

CROSS-REFERENCE TO RELATED APPLICATIONS

This application is a U.S. National Phase application under 35 U.S.C. §371 of International Application Serial No. PCT/JP2014/070154, filed on Jul. 31, 2014, which claims the benefit of Japanese Application Ser. No. 2013-159521, filed on Jul. 31, 2013, both of which are hereby incorporated by reference.

TECHNICAL FIELD

The present invention relates to aminopyrazole derivative-containing pharmaceutical formulations.

BACKGROUND ART

Most of currently promising molecular-targeted drugs against cancer are receptor tyrosine kinase inhibitors such as erlotinib and lapatinib. Many of them are highly effective against cancers with mutation, amplification, or overexpression of target genes. However, such molecular-targeted agents cannot exert efficacy against cancers in which genes that are not their targets are altered. Thus, there is still no established therapeutic method that is effective against such cancers. Inhibitors against novel genes altered in cancer are expected to make a great contribution to treatment of cancer patients on whom conventional drugs have no effect.

Fibroblast growth factor receptors (FGFRs) are kinases belonging to the receptor tyrosine kinase family. FGFR1, FGFR2, FGFR3, and FGFR4 constitute the FGFR family. The ligand is fibroblast growth factor (FGF), and 22 types of structurally similar proteins form a family. It is known that each FGFR is activated upon overexpression, gene amplification, mutation, or translocation, and serves as a cause of cancer. The FGFR signal follows the MAPK pathway or PI3K/AKT pathway. In cancer, the signal is known to be involved in cell growth, angiogenesis, cell migration, invasion, metastasis, and such (Non-patent Document 1).

All such FGFR family kinases have been strongly suggested to be associated with cancer; it is thought that inhibition of these FGFR family kinases in cancer tissues can be a promising therapy for the above-mentioned cancer types.

In this context, Applicants have already provided low-molecular-weight compounds that can inhibit fibroblast growth factor receptor (FGFR) family kinases in cancer tissues (Patent Document 1).

When providing pharmaceuticals, formulations must, for example, be effectively absorbed within the body. Thus, even pyrazole compounds described in Patent Document 1 must be effectively formulated. For example, of formulation forms, encapsulated formulations are administered after enclosing active ingredients (drug substances) in a small space, and therefore, it is important that drug substances are dispersed after capsule disintegration.

PRIOR ART DOCUMENTS

[Patent Document]
 [Patent Document1] WO 2011/016528
Non-Patent Document
 [Non-patent Document 1] Cytokine & Growth Factor Reviews 16 (2005) 139-149

SUMMARY OF THE INVENTION

Problems to be Solved by the Invention

The present inventors attempted to formulate indole ring-containing aminopyrazole compounds used in the present invention. Specifically, formulations manufactured using an unmilled compound of [5-amino-1-(2-methyl-3H-benzimidazol-5-yl)-1H-pyrazol-4-yl]-(1H-indol-2-yl)-methanone (Compound 1 described in Example 1 of the present application) disintegrated and dispersed, but dissolved slowly thereafter due to large particle size. Thus, there were concerns about poor absorption within the body. On the other hand, when the compound was milled, it was found that dissolution was even slower than the unmilled drug substance because grinding increases water-dissolving speed, causing the surface of compound particles to come into contact with water, gel and hind to each other before the capsule completely disintegrates, resulting in ineffective disintegration of encapsulated formulations.

The present inventors further attempted to improve the dissolution properties of formulations by improving manufacturing methods and adding surfactants. However, it was difficult to effectively formulate the compounds, because similarly, drug substances dissolved more quickly, and gelled before disintegration of the formulations, blocking formulation disintegration.

Accordingly an objective of the present invention is to improve the dissolution properties of pharmaceutical formulations containing the aminopyrazole compounds used in the present invention.

Means for Solving the Problems

The present inventors conducted dedicated research to achieve the above objective, and discovered that the aminopyrazole compounds used in the present invention can be prepared into formulations having excellent dissolution properties without gelation of compound particles, by adding alkyl sulfate salts to the formulations, and thus completed the present invention.

Specifically, the present invention includes the following.

[1] pharmaceutical formulation comprising
 an alkyl sulfate salt; and
 a compound represented by general formula (I) below, or a tautomer thereof, or a pharmaceutically acceptable salt thereof:

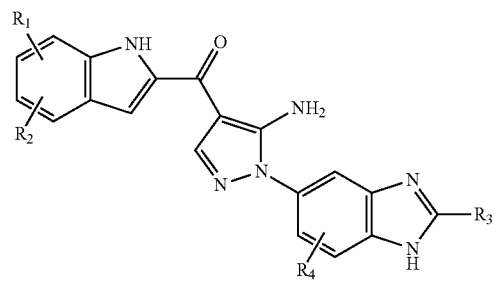

wherein $R_1$ to $R_4$ each independently represents the group listed below:

$R_1$ represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{3-7}$ cycloalkyl, $C_{6-10}$ aryl-$C_{1-4}$ alkyl, —$OR_5$, —$NR_6R_7$, —$(CR_8R_9)_nZ_1$, —$C(O)NR_{12}R_{13}$, —$SR_{14}$, —$SOR_{15}$, —$SO_2R_{16}$, —$NR_{17}SO_2R_{18}$, COOH, $C_{6-10}$ aryl optionally substituted with one or more groups independently selected from Group P, 5- to 10-membered heteroaryl or 3- to 10-membered heterocyclyl optionally substituted with one or more groups independently selected from Group Q, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$;

$R_2$ represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{3-7}$ cycloalkyl, $C_{6-10}$ aryl-$C_{1-4}$ alkyl, —$OR_5$, —$NR_6R_7$, —$(CR_8R_9)_nZ_1$, —$C(O)NR_{12}R_{13}$, —$SR_{14}$, —$SOR_{15}$, —$SO_2R_{16}$, —$NR_{17}SO_2R_{18}$, COOH, $C_{6-10}$ aryl optionally substituted with one or more groups independently selected from Group P, 5- to 10-membered heteroaryl or 3- to 10-membered heterocyclyl optionally substituted with one or more groups independently selected from Group Q, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$; or $R_1$ and $R_2$, together with the atoms to which they are bound, form 3- to 10-membered heterocyclyl or 5- to 10-membered heteroaryl, wherein the heterocyclyl or the heteroaryl is optionally substituted with halogen;

$R_3$ represents hydrogen, $C_{1-5}$ alkyl, $C_{6-10}$ aryl-$C_{1-6}$ alkyl, or $C_{1-4}$ haloalkyl;

$R_4$ represents hydrogen, halogen, $C_{1-3}$ alkyl, $C_{1-3}$ perfluoroalkyl, cyano, methanesulfonyl, hydroxyl, alkoxy, or amino;

$R_5$ represents $C_{1-5}$ alkyl, $C_{3-7}$ cycloalkyl, $C_{3-7}$ cycloalkyl-$C_{1-3}$ alkyl, $C_{2-6}$ alkenyl, $C_{2-6}$ alkynyl, $C_{1-4}$ haloalkyl, $C_{1-3}$ alkoxy-$C_{1-4}$ alkyl, $C_{1-3}$ alkoxy-$C_{1-4}$ alkoxy-$C_{1-4}$ alkyl, $C_{1-4}$ aminoalkyl, $C_{1-4}$ alkylamino-$C_{1-4}$ alkyl, di($C_{1-4}$ alkyl)amino-$C_{1-4}$ alkyl, $C_{6-10}$ aryl, $C_{6-10}$ aryl-$C_{1-3}$ alkyl, 3- to 10-membered heterocyclyl-$C_{1-3}$ alkyl optionally substituted with one or more groups independently selected from Group Q, 3- to 10-membered heterocyclyl, 5- to 10-membered heteroaryl, 5- to 10-membered heteroaryl-$C_{1-3}$ alkyl, $C_{1-6}$ monohydroxyalkyl, $C_{1-6}$ dihydroxyalkyl, or $C_{1-6}$ trihydroxyalkyl;

$R_6$ and $R_7$ are the same or different, and each represents hydrogen, $C_{1-4}$ alkyl, $C_{2-6}$ alkenyl, $C_{2-6}$ alkynyl, $C_{1-4}$ haloalkyl, $C_{1-3}$ alkoxy-$C_{1-4}$ alkyl, $C_{6-10}$ aryl-$C_{1-3}$ alkyl, 3- to 10-membered heterocyclyl-$C_{1-3}$ alkyl, 5- to 10-membered heteroaryl-$C_{1-3}$ alkyl, $C_{1-6}$ monohydroxyalkyl, $C_{1-6}$ dihydroxyalkyl, $C_{1-6}$ trihydroxyalkyl, 3- to 10-membered heterocyclyl, $C_{1-4}$ aminoalkyl, $C_{1-4}$ alkylamino-$C_{1-4}$ alkyl, di($C_{1-4}$ alkyl)amino-$C_{1-4}$ alkyl, or cyano($C_{1-3}$ alkyl); or $R_6$ and $R_7$, together with the nitrogen atom to which they are bound, form 3- to 10-membered heterocyclyl or 5- to 10-membered heteroaryl;

n represents 1 to 3;

$R_8$ and $R_9$ are the same or different, and each represents hydrogen, $C_{1-4}$ alkyl, or halogen; or $R_8$ and $R_9$, together with the carbon atom to which they are bound, form an alicyclic ring;

$Z_1$ represents hydrogen, $NR_{10}R_{11}$, —OH, or 3- to 10-membered heterocyclyl or 5- to 10-membered heteroaryl optionally substituted with one or more groups independently selected from Group Q;

$R_{10}$ and $R_{11}$ are the same or different, and each represents $C_{1-4}$ alkyl, $C_{2-6}$ alkenyl, $C_{2-6}$ alkynyl, $C_{1-4}$ haloalkyl, $C_{1-3}$ alkoxy-$C_{1-4}$ alkyl, cyano($C_{1-3}$ alkyl), or $C_{1-3}$ alkylsulfonyl-$C_{1-4}$ alkyl; or $R_{10}$ and $R_{11}$, together with the nitrogen atom to which they are bound, form 3- to 10-membered heterocyclyl or 5- to 10-membered heteroaryl;

$R_{12}$ and $R_{13}$ are the same or different, and each represents hydrogen, $C_{1-4}$ alkyl, $C_{2-6}$ alkenyl, $C_{2-6}$ alkynyl, $C_{1-4}$ haloalkyl, $C_{1-3}$ alkoxy-$C_{1-4}$ alkyl, $C_{6-10}$ aryl, 5- to 10-membered heteroaryl, 3- to 10-membered heterocyclyl, $C_{6-10}$ aryl-$C_{1-4}$ alkyl, 3- to 10-membered heterocyclyl-$C_{1-3}$ alkyl, 5- to 10-membered heteroaryl-$C_{1-3}$ alkyl, cyano($C_{1-3}$ alkyl), $C_{1-3}$ alkylsulfonyl-$C_{1-4}$ alkyl, a 3- to 10-membered alicyclic ring, 5- to 10-membered heteroaryl, or 3- to 10-membered heterocyclyl; or $R_{12}$ and $R_{13}$, together with the nitrogen atom to which they are bound, form 3- to 10-membered heterocyclyl or 5- to 10-membered heteroaryl optionally substituted with one or more groups independently selected from Group Q;

$R_{14}$ represents $C_{1-4}$ alkyl, $C_{2-6}$ alkenyl, $C_{2-6}$ alkynyl, $C_{1-4}$ haloalkyl, $C_{6-10}$ aryl optionally substituted with one or more groups independently selected from Group P, or 5- to 10-membered heteroaryl or 3- to 10-membered heterocyclyl optionally substituted with one or more groups independently selected from Group Q;

$R_{15}$ represents $C_{1-4}$ alkyl, $C_{2-6}$ alkenyl, $C_{2-6}$ alkynyl, $C_{1-4}$ haloalkyl, $C_{6-10}$ aryl optionally substituted with one or more groups independently selected from Group P, or 5- to 10-membered heteroaryl or 3- to 10-membered heterocyclyl optionally substituted with one or more groups independently selected from Group Q;

$R_{16}$ represents $C_{1-4}$ alkyl, $C_{2-6}$ alkenyl, $C_{2-6}$ alkynyl, $C_{1-4}$ haloalkyl, $C_{6-10}$ aryl optionally substituted with one or more groups independently selected from Group P, or 5- to 10-membered heteroaryl or 3- to 10-membered heterocyclyl optionally substituted with one or more groups independently selected from Group Q;

$R_{17}$ represents hydrogen or $C_{1-4}$ alkyl;

$R_{18}$ represents $C_{1-4}$ alkyl, $C_{2-6}$ alkenyl, $C_{2-6}$ alkynyl, $C_{1-4}$ haloalkyl, $C_{6-10}$ aryl optionally substituted with one or more groups independently selected from Group P, or 5- to 10-membered heteroaryl or 3- to 10-membered heterocyclyl optionally substituted with one or more groups independently selected from Group Q;

$R_{19}$ represents hydrogen, $C_{1-4}$ alkyl, $C_{3-7}$ cycloalkyl, $C_{1-4}$ haloalkyl, $C_{6-10}$ aryl, or 5- to 10-membered heteroaryl or 3- to 10-membered heterocyclyl optionally substituted with one or more groups independently selected from Group Q;

$R_{20}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{21}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{22}$ represents hydrogen, $C_{1-4}$ alkyl, or $C_{1-4}$ haloalkyl;

$R_{23}$ represents hydrogen, $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{24}$ represents hydrogen, $C_{1-4}$ alkyl, or $C_{1-4}$ haloalkyl;

$R_{25}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{26}$ and $R_{27}$ are the same or different, and each represents hydrogen, $C_{1-4}$ alkyl, $C_{2-6}$ alkenyl, $C_{2-6}$ alkynyl, $C_{1-4}$ haloalkyl, $C_{1-2}$ alkoxyl-$C_{1-4}$ alkyl, $C_{6-10}$ aryl, 5- to 10-membered heteroaryl, 3- to 10-membered heterocyclyl, $C_{6-10}$ aryl-$C_{1-4}$ alkyl, 3- to 10-membered heterocyclyl-$C_{1-3}$ alkyl, 5- to 10-membered heteroaryl-$C_{1-3}$ alkyl, cyano($C_{1-3}$ alkyl), $C_{1-3}$ alkylsulfonyl-$C_{1-4}$ alkyl, or a 3- to 10-membered alicyclic ring; or $R_{26}$ and $R_{27}$, together with the nitrogen atom to which they are bound, form 3- to 10-membered heterocyclyl or 5- to 10-membered heteroaryl;

$R_{28}$ and $R_{29}$ are the same or different, and each represents hydrogen, $C_{1-4}$ alkyl, $C_{2-6}$ alkenyl, $C_{2-6}$ alkynyl, $C_{1-4}$ haloalkyl, $C_{1-3}$ alkoxyl-$C_{1-4}$ alkyl, $C_{6-10}$ aryl, 5- to 10-membered heteroaryl, 3- to 10-membered heterocyclyl, $C_{6-10}$ aryl-$C_{1-4}$ alkyl, 3- to 10-membered heterocyclyl-$C_{1-3}$ alkyl, 5- to 10-membered heteroaryl-$C_{1-3}$ alkyl, cyano($C_{1-3}$ alkyl), $C_{1-3}$ alkylsulfonyl-$C_{1-4}$ alkyl, or a 3- to 10-membered alicyclic ring; or $R_{28}$ and $R_{29}$, together with the nitrogen atom to which they are bound, form 3- to 10-membered heterocyclyl or 5- to 10-membered heteroaryl;

$R_{30}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{31}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl; and $R_{32}$ represents $C_{1-4}$ alkyl or $C_{6-10}$ aryl;

<Group P> halogen, $C_{1-4}$ alkyl, $C_{1-4}$ haloalkyl, —OH, $C_{1-3}$ alkoxy, $C_{1-3}$ haloalkoxy, 3- to 10-membered heterocyclylamino, —$SO_2R_{16}$, —CN, —$NO_2$, and 3- to 10-membered heterocyclyl;

<Group Q> halogen, $C_{1-4}$ alkyl, $C_{1-4}$ haloalkyl, —OH, $C_{1-3}$ alkoxy, $C_{1-6}$ monohydroxyalkyl, $C_{1-6}$ dihydroxyalkyl, or $C_{1-6}$ trihydroxyalkyl, 3- to 10-membered heterocyclylamine, —$SO_2R_{16}$, —CN, —$NO_2$, $C_{3-7}$ cycloalkyl, —$COR_{19}$, and 3- to 10-membered heterocyclyl optionally substituted with $C_{1-4}$ alkyl.

[2] The pharmaceutical formulation of [1], wherein $R_3$ is $C_{1-4}$ alkyl.

[3] The pharmaceutical formulation of [1] or [2], wherein $R_4$ is hydrogen.

[4] The pharmaceutical formulation of any one of [1] to [3], wherein $R_1$ and $R_2$ are hydrogen.

[5] The pharmaceutical formulation of any one of [1] to [4], wherein the compound represented by formula (I) is a compound represented by:

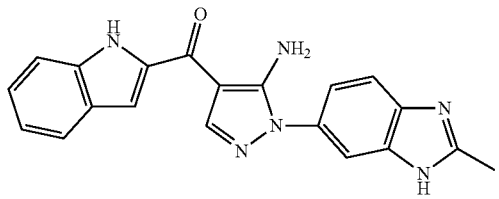 [SMILES: Cc1nc2ccc(-n3ncc(C(=O)c4cc5ccccc5[nH]4)c3N)cc2[nH]1]

or a tautomer thereof.

[6] The pharmaceutical formulation of any one of [1] to [5], wherein the alkyl sulfate salt is a $C_{10-14}$ alkyl sulfate salt.

[7] The pharmaceutical formulation of any one of [1] to [6], wherein the alkyl sulfate salt is a lauryl sulfate salt.

[8] The pharmaceutical formulation of any one of [1] to [7], wherein the pharmaceutical formulation is a solid formulation.

[9] The pharmaceutical formulation of [8], wherein the solid formulation is a capsule, tablet, powder, granule, or dry syrup.

[10] The pharmaceutical formulation of any one of [1] to [9], wherein the compound represented by general formula (I) or a tautomer thereof, or a pharmaceutically acceptable salt thereof is a particle, and wherein the particle has an average particle size of 10 μm or less.

[11] The pharmaceutical formulation of any one of [1] to [10], which further comprises a disintegrant.

[12] The pharmaceutical formulation of [11], wherein the disintegrant is a super disintegrant.

[13] The pharmaceutical formulation of [11], wherein the disintegrant is at least one selected from the group consisting of croscarmellose sodium, carmellose calcium, crospovidone, sodium carboxymethyl starch, low-substituted hydroxypropylcellulose, corn starch, and soybean polysaccharide.

[14] The pharmaceutical formulation of any one of [1] to [13], wherein the pharmaceutical formulation is a capsule, and wherein the compound represented by formula (I) or a tautomer thereof, or a pharmaceutically acceptable salt thereof is comprised in one capsule at a content ratio of 10% by weight or less, in terms of free form, to a total amount of the pharmaceutical formulation excluding the weight of the capsule shell.

[15] The pharmaceutical formulation of [14], wherein one capsule comprises a total amount of 20 mg or more, in terms of free form, of the compound represented by formula (I) or a tautomer thereof, or a pharmaceutically acceptable salt thereof.

[16] The pharmaceutical formulation of any one of [1] to [15], wherein the pharmaceutical formulation is a capsule added with extragranular crystalline cellulose.

[17] The pharmaceutical formulation of any one of [1] to [13], wherein the pharmaceutical formulation is a tablet.

[18] The pharmaceutical formulation of [17], which comprises the compound represented by:

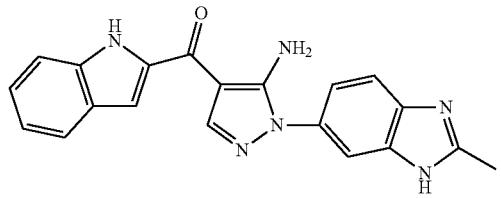 [SMILES: Cc1nc2ccc(-n3ncc(C(=O)c4cc5ccccc5[nH]4)c3N)cc2[nH]1]

or a tautomer thereof, or a pharmaceutically acceptable salt thereof; sodium lauryl sulfate; and a super disintegrant.

[19] The pharmaceutical formulation of [17] or [18], wherein the tablet comprises 1% to 50% by weight of the compound represented by formula (I) or a tautomer thereof, or a pharmaceutically acceptable salt thereof, in terms of free form, to a total amount of the tablet.

[20] The pharmaceutical formulation of any one of [17] to [19], wherein the ratio by weight between the compound represented by formula (I) or a tautomer thereof, or a pharmaceutically acceptable salt thereof and the alkyl sulfate salt is 1:10 to 8:1 in terms of free form of the compound represented by formula (I) or a tautomer thereof, or a pharmaceutically acceptable salt thereof.

[21] The pharmaceutical formulation of any one of [17] to [20], wherein the content by weight of the compound represented by formula (I) or a tautomer thereof, or a pharmaceutically acceptable salt thereof, in terms of free form, is 1 mg to 500 mg.

[22] A method for manufacturing a solid pharmaceutical formulation comprising the pharmaceutical formulation of [1], which comprises the steps of:
providing a mixture comprising an alkyl sulfate salt and the compound represented by general formula (I) described in [1] or a tautomer thereof, or a pharmaceutically acceptable salt thereof;
granulating the mixture without adding water to the mixture, or by adding an amount of purified water to the mixture at 25% by weight or less to a total amount of the mixture; and
providing a dry powder by drying the granulated mixture.
[23] The manufacturing method of [22], which further comprises the steps of:
providing a particle size-granulated powder by subjecting the dry powder to particle size granulation;
providing a compounded powder by mixing the particle size-granulated powder and an additive comprising magnesium stearate; and
preparing the pharmaceutical formulation of any one of [17] to [21] in the form of a tablet by tableting the compounded powder.
[24] Use of an alkyl sulfate salt as an anti-gelation agent for a solid pharmaceutical formulation.
[25] Use of an alkyl sulfate salt as an anti-gelation agent for a solid pharmaceutical formulation comprising the compound represented by formula (I) described in [1] or a tautomer thereof, or a pharmaceutically acceptable salt thereof.
[26] The pharmaceutical formulation of any one of [1] to [21], wherein the pharmaceutical formulation is used for the prevention or treatment of cancer.
[27] A method for preventing or treating cancer, which comprises administering a pharmaceutically effective amount of the pharmaceutical formulation of any one of [1] to [21] to a patient in need of the prevention or treatment of cancer.
[28] Use of the pharmaceutical formulation of any one of [ ] to [21] for the manufacture of a prophylactic or therapeutic agent for cancer.
[29] The pharmaceutical formulation of any one of [1] to [21] for use in the prevention or treatment of cancer.

The present invention also includes "compositions" containing constituents similar to those of the "pharmaceutical formulations" of the present invention, and such "compositions" have effects similar to those of the "pharmaceutical formulations."

Effects of the Invention

The pharmaceutical formulations containing the aminopyrazole compounds used in the present invention contain alkyl sulfate salts, and therefore they have excellent dissolution properties without causing gelation of the compound particles.

MODE FOR CARRYING OUT THE INVENTION

Figure 1:
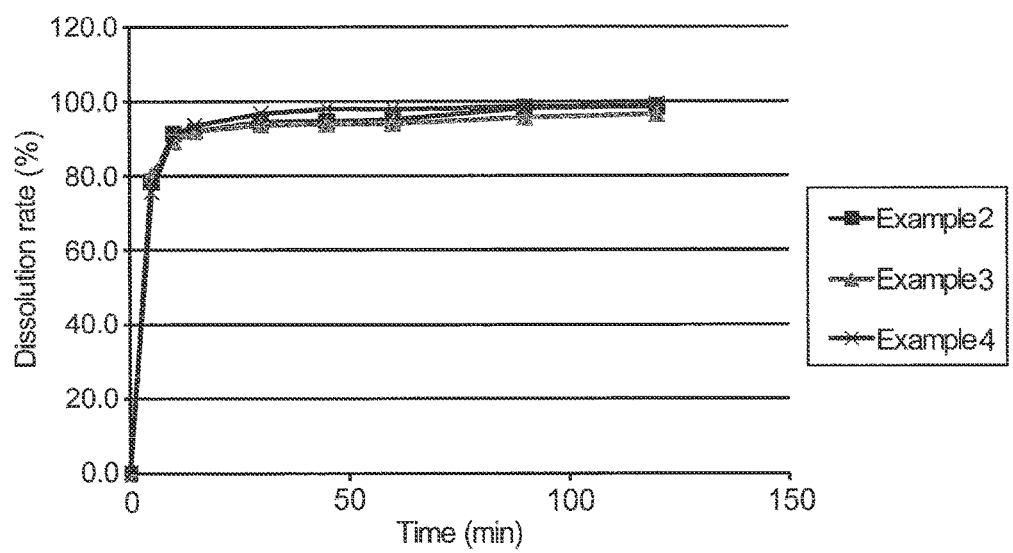
FIG. 1 is a graph showing dissolution profiles for capsules containing a fixed amount (10.0 mg) of sodium lauryl sulfate and 1.0 mg, 5.0 mg, and 10.0 mg of Compound 1 (in terms of free form), respectively (Examples 2, 3, and 4).

The pharmaceutical formulations according to the present invention (which are sometimes called "pharmaceutical compositions") contain alkyl sulfate salts and compounds represented by general formula (I) or tautomers thereof, or pharmaceutically acceptable salts thereof (hereinafter, sometimes called "compounds applied to the present invention").

Compounds or Tautomers Thereof, or Pharmaceutically Acceptable Salts Thereof

Herein, the "alkyl" refers to a monovalent group derived from an aliphatic hydrocarbon by removing an arbitrary hydrogen atom. It contains no heteroatom nor unsaturated carbon-carbon bond in the backbone, and has a subset of hydrocarbyl or hydrocarbon group structures which contain hydrogen and carbon atoms. The alkyl group includes linear and branched structures. Preferred alkyl groups include alkyl groups with one to six carbon atoms ($C_{1-6}$; hereinafter, for example, "$C_{p-q}$" means that the number of carbon atoms is p to q), $C_{1-5}$ alkyl groups, $C_{1-4}$ alkyl groups, and $C_{1-3}$ alkyl groups.

Specifically, the alkyl includes, for example, methyl group, ethyl group, n-propyl group, isopropyl group, n-butyl group, isobutyl group, s-butyl group, t-butyl group, pentyl group, isopentyl group, 2,3-dimethylpropyl group, 3,3-dimethylbutyl group, and hexyl group.

Herein, "alkenyl" refers to a monovalent hydrocarbon group having at least one double bond (two adjacent SP2 carbon atoms), and includes those of linear and branched forms. Depending on the configuration of the double bond and substituents (if any), the geometry of flit double bond can be of entgegen (E) or zusammen (Z), or cis or trans configuration. Preferred alkenyl groups include $C_{2-6}$ alkenyl groups.

Specifically, the alkenyl includes, for example, vinyl group, allyl group, 1-propenyl group, 2-propenyl group, 1-butenyl group, 2-butenyl group (including cis and trans), 3-butenyl group, pentenyl group, and hexenyl group.

Herein, "alkynyl" refers to a monovalent hydrocarbon group having at least one triple bond (two adjacent SP carbon atoms), and includes those of linear and branched forms. Preferred alkynyl groups include $C_{2-6}$ alkynyl groups.

Specifically, the alkynyl includes, for example, ethynyl group, 1-propynyl group, propargyl group, 3-butynyl group, pentynyl group, and hexynyl group.

The alkenyl and alkynyl may each have one, two, or more double bonds or triple bonds.

Herein, "cycloalkyl" refers to a saturated or partially saturated cyclic monovalent aliphatic hydrocarbon group, and includes monocyclic groups, bicyclo rings, and Spiro rings. Preferred cycloalkyl includes $C_{3-7}$ cycloalkyl groups. Specifically, the cycloalkyl group includes, for example, cyclopropyl group, cyclobutyl group, cyclopentyl group, cyclohexyl group, and cycloheptyl group.

Herein, "cycloalkylalkyl" refers to a group its which an arbitrary hydrogen atom of an "alkyl" defined above is substituted with a "cycloalkyl" defined above. Preferred cycloalkylalkyl groups include $C_{3-7}$ cycloalkyl$_{1-3}$ alkyl, and specifically includes for example, cyclopropylmethyl group and cyclopropylethyl group.

Herein. "hetero atom" refers to a nitrogen atom (N), oxygen atom (O); or sulfur atom (S).

Herein, "halogen atom" refers to a fluorine atom, chlorine atom, bromine atom, or iodine atom.

Herein, "haloalkyl" refers to a group in which preferably one to nine, more preferably one to five identical or different "halogen atoms" defined above are linked to an "alkyl" defined above.

Specifically, the haloalkyl includes, for example, chloromethyl group, dichloromethyl group, trichloromethyl group, fluoromethyl group, difluoromethyl group, perfluoroalkyl group (such as trifluoromethyl group and —$CF_2CF_3$), and 2,2,2-trifluoroethyl group.

Herein, "alkoxy" refers to an oxy group linked with an "alkyl" defined above. Preferred alkoxy includes $C_{1-4}$ alkoxy groups and alkoxy groups. Specifically, alkoxy includes, for example, methoxy group, ethoxy group, 1-propoxy group, 2-propoxy group, n-butoxy group, i-butoxy group, sec-butoxy group, and tert-butoxy group.

Herein. "haloalkoxy" refers to a group in which preferably one to nine, more preferably one to five identical or different halogen atoms defined above are linked to an "alkoxy" defined above.

Specifically, the haloalkoxy includes, for example, chloromethoxy group, trichloromethoxy group, and trifluoromethoxy group.

Herein, "aryl" refers to a monovalent aromatic hydrocarbon ring. The aryl preferably includes $C_{6-10}$ aryl. Specifically, the aryl includes, for example, phenyl group and naphthyl groups (for example, 1-naphthyl group and 2-naphthyl group).

Herein, "alicyclic ring" refers to a monovalent non-aromatic hydrocarbon ring. The alicyclic ring may have unsaturated bonds within its ring, and may be a multicyclic group having two or more rings. The carbon atoms constituting the ring may be oxidized to form a carbonyl. The number of atoms constituting an alicyclic ring preferably ranges from three to ten (3- to 10-membered aliphatic ring). The alicyclic ring includes, for example, cycloalkyl rings, cycloalkenyl rings, and cycloalkynyl rings.

Herein, "heteroaryl" refers to a monovalent aromatic heterocyclic group in which the ring-constituting atoms include preferably one to five hetero atoms. The heteroaryl may be partially saturated, and may be a monocyclic or condensed ring (for example, a bicyclic heteroaryl condensed with a benzene ring or monocyclic heteroaryl ring,). The number of ring-constituting atoms preferably ranges from five to ten (5- to 10-membered heteroaryl).

Specifically, the heteroaryl includes, for example, furyl group, thienyl group, pyrrolyl group, imidazolyl group, pyrazolyl group, thiazolyl group, isothiazolyl group, oxazolyl group, isooxazolyl group, oxadiazolyl group, thiadiazolyl group, triazolyl group, tetrazolyl group, pyridyl group, pyrimidyl group, pyridazinyl group, pyrazinyl group, triazinyl group, benzofuranyl group, benzothienyl group, benzothiadiazolyl group, benzothiazolyl group, benzoxazolyl group, benzoxadiazolyl group, benzoimidazolyl group, indolyl group, isoindolyl group, azaindolyl group, indazolyl group, quinolyl group, isoquinolyl group, cinnolinyl group, quinazolinyl group, quinoxalinyl group, benzodioxolyl group, indolidinyl group, and imidazopyridyl group.

Herein, "heterocyclyl'" refers to a non-aromatic monovalent heterocyclic group in which the ring-constituting atoms include preferably one to five hetero atoms. The heterocyclyl may contain double or triple bonds in its ring. The carbon atoms may be oxidized to form carbonyl. The ring may be a monocyclic or condensed ring. The number of the ring-constituting atoms preferably ranges from three to ten (3- to 10-membered heterocyclyl).

Specifically, the heterocyclyl includes, for example, oxetanyl group, dihydrofuryl group, tetrahydrofuryl group, dihydropyranyl group, tetrahydropyranyl group, tetrahydropyridyl group, morpholinyl group, thiomorpholinyl group, pyrrolidinyl group, piperidinyl group, piperazinyl group, pyrazolidinyl group, imidazolinyl group, imidazolidinyl group, oxazolidinyl group, isooxazolidinyl group, thiazolidinyl group, isothiazolidinyl group, thiadiazolidinyl group, azetidinyl group, oxazolidone group, benzodioxanyl group, benzoxazolyl group, dioxolanyl group, and dioxanyl group.

Herein, "arylalkyl" refers to a group in which an arbitrary hydrogen atom in an "alkyl" defined above is substituted with an "aryl" defined above. The arylalkyl preferably includes $C_{6-10}$ aryl $C_{1-4}$ alkyl and $C_{6-10}$ an $C_{1-3}$ alkyl. Specifically, the arylalkyl includes, for example, benzyl group, phenethyl group, and naphthylmethyl group.

Herein, "heteroarylalkyl" refers to a group in which an arbitrary hydrogen atom in an alkyl defined above is substituted with a "heteroaryl" defined above. The heteroarylalkyl preferably includes 5- to 10-membered heteroaryl $C_{1-3}$ alkyl. Specifically, the heteroarylalkyl includes, for example, pyrrolylmethyl group, imidazolylmethyl group, thienylmethyl group, pyridylmethyl group, pyrimidylmethyl group, quinolylmethyl group, and pyridylethyl group.

Herein, "heterocyclylalkyl" refers to a group in which an arbitrary hydrogen atom in an "alkyl" defined above is substituted with a "heterocyclyl" defined above. The heterocyclylalkyl preferably includes 3- to 10-membered heterocyclyl $C_{1-3}$ alkyl. Specifically, the heterocyclylalkyl includes, for example, morpholinomethyl group, morpholinylethyl group, thiomorpholinylmethyl group, pyrrolidinylmethyl group, piperidinylmethyl group, piperazinylmethyl group, piperazinylethyl group, and oxetanylmethyl group.

Herein, "monohydroxyalkyl" refers to a group in which an arbitrary hydrogen atom in an "alkyl" defined above is substituted with a hydroxyl group. The monohydroxyalkyl preferably includes $C_{1-6}$ monohydroxyalkyl and $C_{2-6}$ monohydroxyalkyl. Specifically, the monohydroxyalkyl includes, for example, hydroxymethyl group, 1-hydroxyethyl group, and 2-hydroxyethyl group.

Herein, "dihydroxyalkyl" refers to a group in which two arbitrary hydrogen atoms in an "alkyl" defined above are substituted with two hydroxyl groups. The dihydroxyalkyl preferably includes $C_{1-6}$ dihydroxyalkyl and $C_{2-6}$ dihydroxyalkyl. Specifically, the dihydroxyalkyl includes, for example, 1,2-dihydroxyethyl group, 1,2-dihydroxypropyl group, and 1,3-dihydroxypropyl group.

Herein, "trihydroxyalkyl" refers to a group in which three arbitrary hydrogen atoms in an "alkyl" defined above are substituted with three hydroxyl groups. The trihydroxyalkyl preferably includes $C_{1-6}$ trihydroxyalkyl and $C_{2-6}$ trihydroxyalkyl.

Herein, "alkoxyalkyl" refers to a group in which an arbitrary hydrogen atom in an "alkyl" defined above is substituted with an "alkoxy" defined above. The alkoxyalkyl preferably includes $C_{1-3}$ alkoxy $C_{1-4}$ alkyl and $C_{1-3}$ alkoxy $C_{2-4}$ alkyl. Specifically, the alkoxyalkyl includes, for example, methoxyethyl.

Herein. "alkoxyalkoxyalkyl" refers to a group in which an arbitrary hydrogen atom in the terminal alkyl of an "alkoxyalkyl" defined above is substituted with an "alkoxy" defined above. The alkoxyalkoxyalkyl preferably includes $C_{1-3}$ alkoxy $C_{1-4}$ alkoxy $C_{1-4}$ alkyl and $C_{1-3}$ alkoxy $C_{2-4}$ alkoxy $C_{2-4}$ alkyl.

Herein, "aminoalkyl" refers to a group in which an arbitrary hydrogen atom in an "alkyl" defined above is substituted with an amino group. The aminoalkyl group preferably includes $C_{1-4}$ aminoalkyl and $C_{2-4}$ aminoalkyl.

Herein, "alkylamino" refers to an amino group linked with an "alkyl" defined above. The alkylamino preferably includes $C_{1-4}$ alkylamino.

Herein, "dialkylamino" refers to an amino group linked with two "alkyls" defined above. The two alkyl groups may be same or different. The dialkylamino preferably includes di($C_{1-4}$ alkyl)amino.

Herein, "alkylaminoalkyl" refers to a group in which an arbitrary hydrogen atom in an "alkyl" defined above is substituted with an "alkylamino" defined above. The alkylaminoalkyl preferably includes $C_{14}$ alkylamino $C_{1-4}$ alkyl and $C_{1-4}$ alkylamino $C_{2-4}$ alkyl.

Herein, "dialkylaminoalkyl" refers to a group in which an arbitrary hydrogen atom in an "alkyl" defined above is substituted with a "dialkylamino" defined above. The dialkylaminoalkyl preferably includes di($C_{1-4}$ alkyl)amino $C_{1-4}$ alkyl and di($C_{1-4}$ alkyl)amino $C_{2-4}$ alkyl.

Herein, "heterocyclylamino" refers to an amino group linked with a "heterocyclyl" defined above. The heterocyclylamino preferably includes 3- to 10-membered heterocyclylamino.

Herein, "cyanoalkyl" refers to a group in which an arbitrary hydrogen atom in an "alkyl" defined above is substituted with a cyano group. The cyanoalkyl preferably includes cyano($C_{1-3}$ alkyl).

Herein, alkylsulfonyl'refers to a sulfonyl group linked with an "alkyl" defined above (i.e. alkyl-$SO_2$—). The alkylsulfonyl preferably includes $C_{1-3}$ alkylsulfonyl. Specifically, the alkylsulfonyl includes methylsulfonyl, ethylsulfonyl, n-propylsulfonyl, and i-propylsulfonyl.

Herein, "alkylsulfonylalkyl" refers to a group in which an arbitrary hydrogen atom in an "alkyl" defined above is substituted with an "alkylsulfonyl" defined above. The alkylsulfonylalkyl preferably includes $C_{1-3}$ alkylsulfonyl $C_{1-4}$ alkyl and $C_{1-3}$ alkylsulfonyl $C_{2-4}$ alkyl.

The present invention includes compounds applied to the present invention including free forms and pharmaceutically acceptable salts thereof. Such "salts" include, for example, inorganic acid salts, organic acid salts, inorganic base salts, organic base salts, and acidic or basic amino acid salts.

"Free form" refers to compounds themselves that are no salts, hydrates, solvates, and the like.

Preferred inorganic acid salts include, for example, hydrochloride, hydrobromide, sulfate, nitrate, and phosphate. Preferred organic salts include, for example, acetate, succinate, fumarate, maleate, tartrate, citrate, lactate, malate, stearate, benzoate, methanesulfonate, and p-toluenesulfonate. A particularly preferred salt in the present invention is malate.

Preferred inorganic base salts include, for example, alkali metal salts such as sodium salts and potassium salts; alkali earth metal salts such as calcium salts and magnesium salts; aluminum salts; and ammonium salts. Preferred organic base salts include, for example, diethylamine salts, diethanolamine salts, meglumine salts, and N,N-dibenzylethylenediamine salts.

Preferred acidic amino acid salts include, for example, aspartate and glutamate. Preferred basic amino acid salts include, for example, arginine salts, lysine salts, and ornithine salts.

When the compounds applied to the present invention are left standing in the atmosphere, they may absorb moisture or adsorb water to form hydrates. Such hydrates are also included in the salts of the present invention.

Furthermore, the compounds applied to the present invention may absorb other solvents to form solvates. Such solvates are also included in the salts of the present invention.

All other structurally possible isomers (geometric isomers, optical isomers, stereoisomers, tautomers, etc) of the compounds applied to the present invention and mixtures of such isomers are included in the present invention.

The compounds applied to the present invention may have polymorphic crystalline forms. Such polymorphs are all included in the present invention.

The compounds applied to the present invention include prodrugs thereof. The prodrugs refer to derivatives of the compounds of the present invention which have a chemically or metabolically degradable group, and upon administration to the living body, revert to the original compounds and exhibit the original drug efficacy. The prodrugs include non-covalent complexes and salts.

The compounds applied to the present invention include those in which one or more atoms within the molecule have been replaced with isotopes. Herein, the isotope refers to an atom which has the same atomic number (proton number) but is different in mass number (sum of protons and neutrons). The target atoms to be replaced with an isotope in the compounds of the present invention, include, for example, hydrogen atom, carbon atom, nitrogen atom, oxygen atom, phosphorus atom, sulfur atom, fluorine atom, and chlorine atom. Their isotopes include $^2H$, $^3H$, $^{13}C$, $^{14}C$, $^{15}N$, $^{17}O$, $^{18}O$, $^{31}P$, $^{32}P$, $^{35}S$, $^{18}F$, and $^{36}Cl$. In particular, radioisotopes such as $^3H$ and $^{14}C$, which decay emitting radiation, are useful in in vivo tissue distribution study etc. of pharmaceuticals or compounds. Stable isotopes do not decay are almost constant in abundance, and emit no radiation. For this reason, stable isotopes can be used safely. The compounds of the present invention can be converted into isotope-substituted compounds according to conventional methods by replacing reagents used in synthesis with reagents containing corresponding isotopes.

The following is preferred for the compounds represented by formula (I) according to the present invention.

$R_1$ shown above preferably represents hydrogen, hydroxy, halogen, cyano, $C_{1-4}$ haloalkyl, $C_{1-6}$ alkyl, $C_{2-6}$ alkynyl, $C_{3-7}$ cycloalkyl, $C_{6-10}$ aryl-$C_{1-4}$ alkyl, —$OR_5$, —$NR_6R_7$, —$(CR_8R_9)_nZ_1$, —$C(O)NR_{12}R_{13}$, —$SR_{14}$, —$SO_2R_{16}$, —$NR_{17}SO_2R_{18}$, COOH, $C_{6-10}$ aryl optionally substituted with one or more groups independently selected from Group P, or 5- to 10-membered heteroaryl or 3- to 10-membered heterocyclyl optionally substituted with one or more groups independently selected from Group Q. Specifically, herein, the 5- to 10-membered heteroaryl is particularly preferably an imidazolyl group, a thienyl group, a pyridyl group, a pyridazinyl group, or a pyrazolyl group, and the 3- to 10-membered heterocyclyl is particularly preferably a morpholinyl group, a tetrahydropyridyl group, or a piperidinyl group.

$R_1$ shown above more preferably represents hydrogen.

$R_2$ shown above preferably represents hydrogen, halogen, $C_{1-4}$ haloalkyl, $C_{1-6}$ alkyl, —$OR_5$, $C_{6-10}$ aryl optionally substituted with one or more groups independently selected from Group P, or 5- to 10-membered heteroaryl optionally substituted with one or more groups independently selected from Group Q. Specifically, herein, the 5- to 10-membered heteroaryl is particularly preferably a pyridyl group.

$R_2$ shown above more preferably represents hydrogen.

Preferably, $R_1$ and the $R_2$ shown above, together with the atoms to which they are bound, can form 3- to 10-membered heterocyclyl or 5- to 10-membered heteroaryl. Herein, the heterocyclyl or the heteroaryl may have a halogen atom as a substituent. Specifically, the 3- to 10-membered heterocyclyl formed by $R_1$ and $R_2$ together with the atoms to which they are bound is particularly preferably a dioxolanyl group or a dioxanyl group.

$R_3$ shown above preferably represents hydrogen, $C_{1-5}$ alkyl, $C_{6-10}$ aryl-$C_{1-6}$ alkyl, or $C_{1-4}$ haloalkyl, more preferably hydrogen or $C_{1-4}$ alkyl, still more preferably $C_1$ alkyl, and particularly preferably methyl.

$R_4$ shown above preferably represents hydrogen or halogen, and more preferably hydrogen.

$R_5$ shown above preferably represents $C_{1-5}$ alkyl, $C_{3-7}$ cycloalkyl, $C_{3-7}$ cycloalkyl $C_{1-3}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{1-3}$ alkoxy $C_{1-4}$ alkoxy $C_{1-4}$ alkyl, $C_{1-4}$ amino alkyl, $C_{1-4}$ alkylamino $C_{1-4}$ alkyl, di($C_{1-4}$ alkyl)amino $C_{1-4}$ alkyl, $C_{6-10}$ aryl, $C_{6-10}$ aryl $C_{1-3}$ alkyl, or 3- to 10-membered heterocyclyl $C_{1-3}$ alkyl, 3- to 10-membered heterocyclyl, 5- to 10-membered heteroaryl, or 5- to 10-membered heteroaryl $C_{1-3}$ alkyl, each of which is optionally substituted with one or more groups independently selected from group Q, $C_{1-6}$ monohydroxyalkyl, $C_{1-6}$ dihydroxyalkyl, or $C_{1-6}$ trihydroxyalkyl.

$R_5$ shown above more preferably represents $C_{1-5}$ alkyl, $C_{3-7}$ cycloalkyl $C_{1-3}$ alkyl, $C_{1-4}$ haloalkyl, $C_{1-3}$ alkoxy $C_{1-4}$ alkyl, $C_{6-10}$ aryl, $C_{6-10}$ aryl $C_{1-3}$ alkyl, or 3- to 10-membered heterocyclyl $C_{1-3}$ alkyl or 3- to 10-membered heterocyclyl each of which is optionally substituted with one or more groups independently selected from group Q. Specifically, the above 3- to 10-membered heterocyclylalkyl is particularly preferably a piperazinylethyl group, oxetanylmethyl group, or morpholinylethyl group. The above 3- to 10-membered heterocyclyl is particularly preferably an oxetanyl group or tetrahydropyranyl group.

$R_6$ and $R_7$ shown above may be the same or different, and each preferably represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{2-4}$ alkyl, $C_{6-10}$ aryl $C_{1-3}$ alkyl, 3- to 10-membered heterocyclyl $C_{1-3}$ alkyl, 5- to 10-membered heteroaryl $C_{1-3}$ alkyl, $C_{1-6}$ monohydroxyalkyl, $C_{1-6}$ dihydroxyalkyl, $C_{1-6}$ trihydroxyalkyl, 3- to 10-membered heterocyclyl, $C_{1-4}$ aminoalkyl, $C_{1-4}$ alkylamino $C_{1-4}$ alkyl, di($C_{1-4}$ alkyl)amino $C_{1-4}$ alkyl, or cyano ($C_{1-3}$ alkyl).

$R_6$ and $R_7$ shown above more preferably each independently represent hydrogen, $C_{1-3}$ alkoxy $C_{1-4}$ alkyl, 3- to 10-membered heterocyclyl $C_{1-3}$ alkyl, 5- to 10-membered heteroaryl $C_{1-3}$ alkyl, or $C_{1-6}$ dihydroxyalkyl. Specifically, the 3- to 10-membered heterocyclylalkyl is particularly preferably a morpholinylethyl group, and the 5- to 10-membered heteroarylalkyl is particularly preferably a pyridylethyl group.

Alternatively, $R_6$ and $R_7$ shown above can preferably be taken together with the nitrogen atoms to which they are bound to form 3- to 10-membered heterocyclyl or 5- to 10-membered heteroaryl.

"n" shown above represents an integer from 1 to 3. Preferably, n is 1.

$R_8$ and $R_9$ shown above preferably may be the same or different, and each represents hydrogen, $C_{1-4}$ alkyl, or halogen, and more preferably hydrogen.

Alternatively, $R_8$ and $R_9$ shown above can preferably be taken together with the carbon atoms to which they are bound to form an alicyclic ring.

$Z_1$ shown above preferably represents hydrogen, $NR_{10}R_{11}$, —OH, or 3- to 10-membered heterocyclyl or 5- to 10-membered heteroaryl each of which is optionally substituted with one or more groups independently selected from group Q, more preferably $NR_{10}R_{11}$ or —OH, or 3- to 10-membered heterocyclyl which is optionally substituted with one or more groups independently selected from group Q. Specifically, the above 3- to 10-membered heterocyclyl is particularly preferably a pyrrolidinyl group, piperazinyl group, piperidinyl group, or morpholinyl group.

$R_{10}$ and $R_{11}$ shown above preferably may be the same or different, and each preferably represents $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, cyano($C_{1-3}$ alkyl), or $C_{1-3}$ alkylsulfonyl $C_{1-4}$ alkyl, more preferably $C_{1-4}$ alkyl, $C_{2-6}$ alkynyl, or $C_{1-3}$ alkoxy $C_{2-4}$ alkyl.

Alternatively, $R_{10}$ and $R_{11}$ shown above can preferably be taken together with the nitrogen atoms to which they are bound to form 3- to 10-membered heterocyclyl or 5- to 10-membered heteroaryl.

$R_{12}$ and $R_{13}$ shown above preferably may be the same or different, and each represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, or 3- to 10-membered alicyclic ring, more preferably hydrogen, $C_{1-4}$ alkyl, or $C_{1-4}$ haloalkyl.

Alternatively, $R_{12}$ and $R_{13}$ shown above preferably can be taken together with the nitrogen atoms to which they are bound to form 3- to 10-membered heterocyclyl or 5- to 10-membered heteroaryl each of which is optionally substituted with one or more groups independently selected from group Q, and particularly preferably 3- to 10-membered heterocyclylalkyl. Specifically, piperazinyl group, morpholinyl group, pyrrolidinyl group, and piperidinyl group are more preferred.

$R_{14}$ shown above preferably represents $C_{1-4}$ alkyl, $C_{2-6}$ alkenyl, $C_{2-6}$ alkynyl, $C_{1-4}$ haloalkyl, $C_{6-10}$ aryl which is optionally substituted with one or more groups independently selected from group P, or 5- to 10-membered heteroaryl or 3- to 10-membered heterocyclyl each of which is optionally substituted with one or more groups independently selected from group Q, and more preferably represents $C_{1-4}$ alkyl or $C_{1-4}$ haloalkyl.

$R_{15}$ shown above preferably represents $C_{1-4}$ alkyl, $C_{2-6}$ alkenyl, $C_{2-6}$ alkynyl, $C_{1-4}$ haloalkyl, $C_{6-10}$ aryl which is optionally substituted with one or more groups independently selected from group P, or 5- to 10-membered heteroaryl or 3- to 10-membered heterocyclyl each of which is optionally substituted with one or more groups independently selected from group Q.

$R_{16}$ shown above preferably represents $C_{1-4}$ alkyl, $C_{2-6}$ alkenyl, $C_{2-6}$ alkynyl, $C_{1-4}$ haloalkyl, $C_{6-10}$ aryl which is optionally substituted with one or more groups independently selected from group P, or 5- to 10-membered heteroaryl or 3- to 10-membered heterocyclyl each of which is optionally substituted with one or more groups independently selected from group Q, and more preferably represents $C_{1-4}$ alkyl.

$R_{17}$ shown above preferably represents hydrogen or $C_{1-4}$ alkyl, and more preferably hydrogen.

$R_{18}$ shown above preferably represents $C_{1-4}$ alkyl, $C_{2-6}$ alkenyl, $C_{2-6}$ alkynyl, $C_{1-4}$ haloalkyl, $C_{6-10}$ aryl which is optionally substituted with one or more groups independently selected from group P, or 5- to 10-membered heteroaryl or 3- to 10-membered heterocyclyl each of which is optionally substituted with one or more groups independently selected from group Q, and more preferably represents $C_{1-4}$ alkyl.

$R_{19}$ shown above preferably represents hydrogen, $C_{1-4}$ alkyl, $C_{3-7}$ cycloalkyl, $C_{1-4}$ haloalkyl, $C_{6-10}$ aryl, or 5- to 10-membered heteroaryl or 3- to 10-membered heterocyclyl each of which is optionally substituted with one or more groups independently selected from group Q, and more preferably represents hydrogen, or 5- to 10-membered heteroaryl or 3- to 10-membered heterocyclyl each of which is optionally substituted with one or more groups independently selected from group Q. Specifically, this 3- to 10-membered heterocyclyl is more preferably a piperazinyl group, morpholinyl group, pyrrolidinyl group, or piperidinyl group.

$R_{20}$ shown above preferably represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl, $R_{21}$ shown above preferably represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl.

$R_{22}$ shown above preferably represents hydrogen, $C_{1-4}$ alkyl, or $C_{1-4}$ haloalkyl.

$R_{23}$ shown above preferably represents hydrogen, $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl.

$R_{24}$ shown above preferably represents hydrogen, $C_{1-4}$ alkyl, or $C_{1-4}$ haloalkyl, $R_{25}$ shown above preferably represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl.

$R_{26}$ and $R_{27}$ shown above preferably may be the same or different, and each represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{6-10}$ aryl, 5- to 10-membered heteroaryl, 3- to 10-membered heterocyclyl, $C_{6-40}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, or 3- to 10-membered alicyclic ring.

Alternatively, $R_{26}$ and $R_{27}$ shown above can preferably be taken together with the nitrogen atoms to which they are bound to form 3- to 10-membered heterocyclyl or 5- to 10-membered heteroaryl.

$R_{28}$ and $R_{29}$ shown above preferably may be the same or different, and each represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, or 3- to 10-membered alicyclic ring.

Alternatively, $R_{28}$ and $R_{29}$ shown above preferably can be taken together with the nitrogen atoms to which they are bound to form 3- to 10-membered heterocyclyl or 5- to 10-membered heteroaryl.

$R_{30}$ shown above preferably represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl.

$R_{31}$ shown above preferably represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl.

$R_{32}$ shown above preferably represents $C_{1-4}$ alkyl, or $C_{6-10}$ aryl.

Preferred substituents included in group P defined above are halogen, $C_{1-4}$ alkyl, $C_{1-4}$ haloalkyl, —OH, $C_{1-3}$ alkoxy, haloalkoxy, 3- to 10-membered heterocyclylamino, —SO$_2$R, —CN, —NO$_2$ and 3- to 10-membered heterocyclyl; and more preferably halogen, $C_{1-4}$ haloalkyl, $C_{1-3}$ alkoxy, $C_{1-3}$ haloalkoxy, and 3- to 10-membered heterocyclyl. Specifically, this 3- to 10-membered heterocyclyl is particularly preferably a morpholinyl group.

Preferred substituents included in group Q defined above are halogen, $C_{1-4}$ alkyl, $C_{1-4}$ haloalkyl, —OH, $C_{1-3}$ alkoxy, $C_{1-6}$ monohydroxyalkyl, $C_{1-6}$ dihydroxyalkyl, $C_{1-6}$ trihydroxyalkyl, 3- to 10-membered heterocyclylamino, —SO$_2$R, —CN, —NO$_2$, $C_{3-7}$ cycloalkyl, —COR$_{19}$, and 3- to 10-membered heterocyclyl which is optionally substituted with $C_{1-4}$ alkyl; and more preferably halogen, $C_{1-4}$ alkyl, $C_{1-4}$ haloalkyl, —OH, $C_{1-3}$ alkoxy, $C_{1-6}$ monohydroxyalkyl, —SO$_2$R$_{16}$, $C_{3-7}$ cycloalkyl, —COR$_{19}$, and 3- to 10-membered heterocyclyl which is optionally substituted with $C_{1-4}$ alkyl. Specifically, this 3- to 10-membered heterocyclyl is more preferably a piperazinyl group, piperidinyl group, or morpholinyl group.

Specific examples of the compound applied to the present invention include the following compounds:

(1) [5-amino-1-(2-methyl-1H-benzimidazol-5-yl)-1H-pyrazol-4-yl]-(1H-indol-2-yl)-methanone (or [5-amino-1-(2-methyl-1H-benzimidazol-5-yl)-1H-pyrazol-4-yl]-(1H-indol-2yl)-methanone);

(2) [5-amino-1-(2-methyl-1H-benzimidazol-5-yl)-1H-pyrazol-4-yl]-(6-pyrrolidin-1-ylmethyl-1H-indol-2-yl)-methanone;

(3) [5-amino-1-(2-methyl-1H-benzimidazol-5-yl)-1H-pyrazol-4-yl]-[6-(4-hydroxy-piperidin-1-ylmethyl)-1H-indol-2-yl]-methanone;

(5) [5-amino-1-(2-methyl-1H-benzimidazol-5-yl)-1H-pyrazol-4-yl]-(6-piperazin-1-ylmethyl-1H-indol-2-yl)-methanone;

(6) [5-amino-1-(2-methyl-1H-benzimidazol-5-yl)-1H-pyrazol-4-yl]-[6-(2-morpholin-4-yl-ethoxy)-1H-indol-2-yl]-methanone;

(7) [5-amino-1-(2-methyl-1H-benzimidazol-5-yl)-1H-pyrazol-4-yl]-[6-(tetrahydro-pyran-4-yloxy)-1H-indol-2-yl]-methanone;

(8) [5-amino-1-(2-methyl-1H-benzimidazol-5-yl)-1H-pyrazol-4-yl]-(4-chloro- H-indol-2-yl)-methanone;

(9) [5-amino-1-(2-methyl-1H-benzimidazol-5-yl)-1H-pyrazol-4-yl]-(5-bromo-1H-indol-2-yl)-methanone;

(10) [5-amino-1-(2-methyl-1H-benzimidazol-5-yl)-1H-pyrazol-4-yl]-(4-iodo-1H-indol-2-yl)-methanone;

(11) 2-[5-amino-1-(2-methyl-1H-benzimidazol-5-yl)-1H-pyrazole-4-carbonyl]-1H-indole-5-carbonitrile;

(12) [5-amino-1-(2-methyl-1H-benzimidazol-5-yl)-1H-pyrazol-4-yl]-(6-bromo-5-fluoro-1H-indol-2-yl)-methanone;

(13) [5-amino-1-(2-methyl-1H-benzimidazol-5-yl)-1H-pyrazol-4-yl]-(5-ethynyl-1H-indol-2-yl)-methanone;

(14) [5-amino-1-(2-methyl-1H-benzimidazol-5-yl)-1H-pyrazol-4-yl]-[6-(2-fluoro-phenyl)-1H-indol-2-yl]-methanone;

(15) [5-amino-1-(2-methyl-1H-benzimidazol-5-yl)-1H-pyrazol-4-yl]-[6-(3-fluoro-phenyl)-1H-indol-2-yl]-methanone;

(16) [5-amino-1-(2-methyl-1H-benzimidazol-5-yl)-1H-pyrazol-4-yl]-[6-(4-fluoro-phenyl)-1H-indol-2-yl]-1-methanone;

(17) [5-amino-1-(2-methyl-1H-benzimidazol-5-yl)-1H-pyrazol-4-yl]-[6-(2-chloro-phenyl)-1H-indol-2-yl]-methanone;

(18) [5-amino-1-(2-methyl-1H-benzimidazol-5-yl)-1H-pyrazol-4-yl]-[6-(3-chloro-phenyl)-1H-indol-2-yl]-methanone;

(19) [5-amino-1-(2-methyl-1H-benzimidazol-5-yl)-1H-pyrazol-4-yl]-[6-(4-chloro-phenyl)-1H-indol-2-yl]-methanone;

(20) [5-amino-1-(2-methyl-1H-benzimidazol-5-yl)-1H-pyrazol-4-yl]-[6-(2-trifluoromethyl -phenyl)-1H-indol-2-yl]-methanone;
(21) [5-amino-1-(2-methyl-1H-benzimidazol-5-yl)-1H-pyrazol-4-yl]-[6-(3-trifluoromethyl -phenyl)-1H-indol-2-yl]-methanone;
(22) [5-amino-1-(2-methyl-1H-benzimidazol-5-yl)-1H-pyrazol-4-yl]-[6-(4-trifluoromethyl -phenyl)-1H-indol-2-yl]-methanone;
(23) [5-amino-1-(2-methyl-1H-benzimidazol-5-yl)-1H-pyrazol-4-yl]-(4-bromo-1H-indol-2-yl)-methanone;
(24) [5-amino-1-(2-methyl-1H-benzimidazol-5-yl)-1H-pyrazol-4-yl]-[6-(3-fluoro-pyridin-2-yl)-1H-indol-2-yl]-methanone;
(25) [5-amino-1-(2-methyl-1H-benzimidazol-5-yl)-1H-pyrazol-4-yl]-(6-methyl-1-indol-2-yl)-methanone;
(26) [5-amino-1-(2-methyl-1H-benzimidazol-5-yl)-1H-pyrazol-4-yl]-[5-(4,4-difluoro-piperidine-1-carbonyl)-1H-indol-2-yl]-methanone;
(27) [5-amino-1-(2-methyl-1H-benzimidazol-5-yl)-1H-pyrazol-4-yl]-[5-(3,3-difluoro-piperidine-1-carbonyl)-1H-indol-2-yl]-methanone;
(28) 2-[5-amino-1-(2-methyl-1H-benzimidazol-5-yl)-1H-pyrazole-4-carbonyl]-1H-indole-5-carboxylic acid (2,2,2-trifluoro-ethyl)-amide;
(29) [5-amino-1-(2-methyl-1H-benzimidazol-5-yl)-1H-pyrazol-4-yl]-[6-(5-trifluoromethyl-pyridin-2-yl)-1H-indol-2-yl]-methanone;
(30) [5-amino-1-(2-methyl-1H-benzimidazol-5-yl)-1H-pyrazol-4-yl]-[6-(6-trifluoromethyl-pyridin-2-yl)-1H-indol-2-yl]-methanone;
(31) [5-amino-1-(2-methyl-1H-benzimidazol-5-yl)-1H-pyrazol-4-yl]-[6-(5-chloro-pyridin-2-yl)-1H-indol-2-yl]-methanone;
(32) [5-amino-1-(2-methyl-1H-benzimidazol-5-yl)-1H-pyrazol-4-yl]-[6-(4-methyl-pyridin-2-yl)-1H-indol-2-yl]-methanone;
(33) [5-amino-1-(2-methyl-1H-benzimidazol-5-yl)-1H-pyrazol-4-yl]-[6-(3-chloro-4-fluoro-phenyl)-1H-indol-2-yl]-methanone;
(34) [5-amino-1-(2-methyl-1H-benzimidazol-5-yl)-1H-pyrazol-4-yl]-[6-(3-trifluoromethyl-pyridin-2-yl)-1H-indol-2-yl]-methanone;
(35) [5-amino-1-(2-methyl-1H-benzimidazol-5-yl)-1H-pyrazol-4-yl]-[6-(4-trifluoromethyl-pyridin-2-yl)-1H-indol-2-yl]methanone;
(36) [5-amino-1-(6-fluoro-2-methyl-1H-benzimidazol-5-yl)-1H-pyrazol-4-yl]-(1H-indol-2-yl)-methanone;
(37) 2-[5-amino-1-(2-methyl-1H-benzimidazol-5-yl)-1H-pyrazole-4-carbonyl]-1H-indole-6-carboxylic acid;
(38) [5-amino-1-(2-methyl-1H-benzimidazol-5-yl)-1H-pyrazol-4-yl]-(6-hydroxymethyl-1H-indol-2-yl)-methanone;
(39) [5-amino-1-(2-methyl-1H-benzimidazol-5-yl)-1H-pyrazol-4-yl]-{6-[2-(4-methyl-piperazin-1-yl-ethoxy]-1H-indol-2-yl}-methanone;
(40) [5-amino-1-(2-methyl-1H-benzimidazol-5-yl)-1H-pyrazol-4-yl]-[6-(3-methyl-oxetan-3-ylmethoxy)-1H-indol-2-yl]-methanone;
(41) [5-amino-1-(2-methyl-1H-benzimidazol-5-yl)-1H-pyrazol-4-yl]-[6-(3-fluoro-piperidin-1-ylmethyl)-1H-indol-2-yl]-methanone;
(42) [5-amino-1-(2-methyl-1H-benzimidazol-5-yl)-1H-pyrazol-4-yl]-(6-{[bis(2-methoxy-ethyl)-amino]-methyl}-1H-indol-2-yl)-methanone;
(43) [5-amino-1-[(2-methyl-1H-benzimidazol-5-yl)-1H-pyrazol-4-yl]-{(methyl-prop-2-ynyl -amino)-methyl]-1H-indol-2-yl}-methanone; (44) [5-amino-1-(2-methyl-1H-benzimidazol-5-yl)-1H-pyrazol-4-yl]-[6-(3,3-difluoro-pyrrolidin-1-ylmethyl)-1H-indol-2-yl]-methanone;
(45) [5-amino-1-(2-methyl-1H-benzimidazol-5-yl)-1H-pyrazol-4-yl]-[6-(2,5-dimethyl-pyrrolidin-1-ylmethyl)-1H-indol-2-yl]-methanone;
(46) [5-amino-1-(2-methyl-1H-benzimidazol-5-yl)-1H-pyrazol-4-yl]-[6-(3,3-difluoro-piperidin-1-ylmethyl)-1H-indol-2-yl]-methanone;
(47) [5-amino-1-(2-methyl-1H-benzimidazol-5-yl)-1H-pyrazol-4-yl]-[6-((S)-3-methyl-morpholin-4-ylmethyl)-1H-indol-2-yl]-methanone;
(48) [5-amino-1-(2-methyl-1H-benzimidazol-5-yl)-1H-pyrazol-4-yl]-(6-bromo-1H-indol-2-yl)-methanone;
(49) [5-amino-1-(2-methyl-1H-benzimidazol-5-yl)-1H-pyrazol-4-yl]-(5-iodo-1H-indol-2-yl)-methanone;
(51) [5-amino-1-(2-methyl-1H-benzimidazol-5-yl)-1H-pyrazol-4-yl]-(5-bromo-6-trifluoromethyl-1H-indol-2-yl)-methanone;
(52) [5-amino-1-(2-methyl-1H-benzimidazol-5-yl)-1H-pyrazol-4-yl]-(6-iodo-1H-indol-2-yl)-methanone;
(53) [5-amino-1-(2-methyl-1H-benzimidazol-5-yl)-1H-pyrazol-4-yl]-(4-methyl-1H-indol-2-yl)-methanone;
(54) [5-amino-1-(2-methyl-1H-benzimidazol-5-yl)-1H-pyrazol-4-yl]-(4-isopropyl-1H-indol-2-yl)-methanone;
(55) [5-amino-1-(2-methyl-1H-benzimidazol-5-yl)-1H-pyrazol-4-yl]-[5-(2-fluoro-phenyl)-1H-indol-2-yl]-methanone;
(56) [5-amino-1-(2-methyl-1H-benzimidazol-5-yl)-1H-pyrazol-4-yl]-(5-benzyl-1H-indol-2-yl)-methanone;
(57) [5-amino-1-(2-methyl-1H-benzimidazol-5-yl)-1H-pyrazol-4-yl]-[5-(2-trifluoromethyl-phenyl)-1H-indol-2-yl]-methanone;
(58) [5-amino-1-(2-methyl-1H-benzimidazol-5-yl)-1H-pyrazol-4-yl]-[5-(3-fluorophenyl)-1H -indol-2-yl]-methanone;
(59) [5-amino-1-(2-methyl-1H-benzimidazol-5-yl)-1H-pyrazol-4-yl]-[5-(3-trifluoromethyl-phenyl)-1H-indol-2-yl]-methanone;
(60) [5-amino-1-(2-methyl-1H-benzimidazol-5-yl)-1H-pyrazol-4-yl]-(4-ethynyl-1H-indol-2-yl)-methanone;
(61) [5-amino-1-(2-methyl-1H-benzimidazol-5-yl)-1H-pyrazol-4-yl]-(5H-[1,3]dioxolo[4,5-f]indol-6-yl)-methanone;
(62) [5-amino-1-(2-methyl-1H-benzimidazol-5-yl)-1H-pyrazol-4-yl]-(1H-indol-2-yl)-methanone;
(63) [5-amino-1-(2-methyl-1H-benzimidazol-5-yl)-1H-pyrazol-4-yl]-[5-(4-trifluoromethyl-phenyl)-1H-indol-2-yl]-methanone;
(64) [5-amino-1-(2-methyl-1H-benzimidazol-5-yl)-1H-pyrazol-4-yl]-(5-butoxy-1H-indol-2-yl)-methanone;
(65) [5-amino-1-(2-methyl-1H-benzimidazol-5-yl)-1H-pyrazol-4-yl]-[5-(1-methyl-piperidin-4-yl)-1H-indol-2-yl]methanone;
(66) N-{2-[5-amino-1-(2-methyl-1H-benzimidazol-5-yl)-1H-pyrazol-4-carbonyl]-1H-indol-6-yl}-methanesulfonamide;
(67) [5-amino-1-(2-methyl-1H-benzimidazol-5-yl)-1H-pyrazol-4-yl]-[6-(6-morpholin-4-yl-pyridin-3-yl)-1H-indol-2-yl]-methanone;
(68) [5-amino-1-(2-methyl-1H-benzimidazol-5-yl)-1H-pyrazol-4-yl]-(6-butyl-1H-indol-2-yl)-methanone;
(69) [5-amino-1-(2-methyl-1H-benzimidazol-5-yl)-1H-pyrazol-4-yl]-[6-(1-methyl-1H-pyrazol-4-yl)-1H-indol-2-yl]-methanone;

(70) [5-amino-1-(2-methyl-1H-benzimidazol-5-yl)-1H-pyrazol-4-yl]-[6-(5-methoxy-pyridin-3-yl)-1H-indol-2-yl]-methanone;
(71) [5-amino-1-(2-methyl-1H-benzimidazol-5-yl)-1H-pyrazol-4-yl]-[6-(2-methoxy-pyridin-3-yl)-1H-indol-2-yl]-methanone;
(72) [5-amino-1-(2-methyl-1H-benzimidazol-5-yl)-1H-pyrazol-4-yl]-(6-cyclopropyl-1H-indol-2-yl)-methanone;
(73) [5-amino-1-(2-methyl-1H-benzimidazol-5-yl)-1H-pyrazol-4-yl]-[6-(2-methoxy-phenyl-(1H-indol-2-yl]-methanone;
(74) [5-amino-1-(2-methyl-1H-benzimidazol-5-yl)-1H-pyrazol-4-yl]-(6-phenyl-1H-indol-2-yl)-methanone;
(75) [5-amino-1-(2-methyl-1H-benzimidazol-5-yl)-1H-pyrazol-4-yl]-[6-(5-methanesulfonyl-pyridin-3-yl)-1H-indol-2-yl]-methanone;
(76) [5-amino-1-(2-methyl-1H-benzimidazol-5-yl)-1H-pyrazol-4-yl]-(6-isopropyl-1H-indol-2-yl)-methanone;
(77) [5-amino-1-(2-methyl-1H-benzimidazol-5-yl)-1H-pyrazol-4-yl]-(6-pyridin-2-yl-1H-indol-2-yl)-methanone;
(78) [5-amino-1-(2-methyl-1H-benzimidazol-5-yl)-1H-pyrazol-4-yl]-(5-cyclopropyl-1H-indol-2-yl)-methanone;
(79) [5-amino-1-(2-methyl-1H-benzimidazol-5-yl)-1H-pyrazol-4-yl]-(6-pyridazin-3-yl-1H-indol-2-yl)-methanone;
(80) [5-amino-1-(2-methyl-1H-benzimidazol-5-yl)-1H-pyrazol-4-yl]-(5-isopropoxy-1H-indol-2-yl)-methanone;
(81) [5-amino-1-(2-methyl-1H-benzimidazol-5-yl)-1H-pyrazol-4-yl]-[5-(2-methoxy-ethoxy)-1H-indol-2-yl]-methanone;
(82) [5-amino-1-(2-methyl-1H-benzimidazol-5-yl)-1H-pyrazol-4-yl]-(5-cyclopropylmethoxy-1H-indol-2-yl)-methanone;
(83) [5-amino-1-(2-methyl-1H-benzimidazol-5-yl)-1H-pyrazol-4-yl]-(2,2-difluoro-5H-[1,3]dioxolo[4,5-f]indol-6-yl)-methanone;
(84) [5-amino-1-(2-methyl-1H-benzimidazol-5-yl)-1H-pyrazol-4-yl]-[6-(3-chloro-pyridin-2-yl)-1H-indol-2-yl]-methanone;
(85) [5-amino-1-(2-methyl-1H-benzimidazol-5-yl)-1H-pyrazol-4-yl]-[6-(5-fluoro-pyridin-2-yl)-1H-indol-2-yl]-methanone;
(86) [5-amino-1-(2-methyl-1H-benzimidazol-5-yl)-1H-pyrazol-4-yl]-[6-6-morpholin-4-yl-pyridazin-3-yl)-1H-indol-2-yl]-methanone;
(87) [5-amino-1-(2-methyl-1H-benzimidazol-5-yl)-1H-pyrazol-4-yl]-(5-chloro-6-cyclopropylmethoxy-1H-indol-2-yl)-methanone;
(88) [5-amino-1-(2-methyl-1H-benzimidazol-5-yl)-1H-pyrazol-4-yl]-[6-(2,4-difluoro-phenyl)-1H-indol-2-yl]-methanone;
(89) [5-amino-1-(2-methyl-1H-benzimidazol-5-yl)-1H-pyrazol-4-yl]-(6-pyridazin-4-yl-1H-indol-2-yl)-methanone;
(90) [5-amino-1-(2-methyl-1H-benzimidazol-5-yl)-1H-pyrazol-4-yl]-(3-fluoro-1H-indol-2-yl)-methanone;
(91) [5-amino-1-(2-methyl-1H-benzimidazol-5-yl)-1H-pyrazol-4-yl]-[5-(1-isopropyl-piperidin-4-yl)-6-trifluoromethyl-1H-indol-2-yl]-methanone;
(92) [5-amino-1-(2-methyl-1H-benzimidazol-5-yl)-1H-pyrazole-4-carbonyl]-1H-indole-6-carbonitrile;
(93) [5-amino-1-(2-methyl-1H-benzimidazol-5-yl)-1H-pyrazol-4-yl]-[5-(1,2,3,6-tetrahydro-pyridin-4-yl)-1H-indol-2-yl]-methanone;
(94) [5-amino-1-(2-methyl-1H-benzimidazol-5-yl)-1H-pyrazol-4-yl]-(5-piperidin-4-yl-1H-indol-2-yl)-methanone;
(95) [5-amino-1-(2-methyl-1H-benzimidazol-5-yl)-1H-pyrazol-4-yl]-[5((R)-3-fluoro-pyrrolidin-1-ylmethyl)-1H-indol-2-yl]-methanone;
(96) [5-amino-1-(2-methyl-1H-benzimidazol-5-yl)-1H-pyrazol-4-yl]-(6-fluoro-5-piperidin-4-yl-1H-indol-2-yl)-methanone;
(97) [5-amino-1-(2-methyl-1H-benzimidazol-5-yl)-1H-pyrazol-4-yl]-[6-fluoro-5-(1-methyl-piperidin-4-yl)-1H-indol-2-yl]-methanone;
(98) [5-amino-1-(2-methyl-1H-benzimidazol-5-yl)-1H-pyrazol-4-yl]-[5-(1-isopropyl-piperidin-4-yl)-1H-indol-2-yl]-methanone;
(99) [5-amino-1-(2-methyl-1H-benzimidazol-5-yl)-1H-pyrazol-4-yl]-[6-fluoro-5(1-isopropyl-piperidin-4-yl)-1H-indol-2-yl]-methanone;
(100) [5-amino-1-(2-methyl-1H-benzimidazol-5-yl)-1H-pyrazol-4-yl]-(6-pyridin-3-yl-1H-indol-2-yl)-methanone;
(101) [5-amino-1-(2-methyl-1H-benzimidazol-5-yl)-1H-pyrazol-4-yl]-[5-(6-morpholin-4-yl-pyridin-3-yl)-1H-indol-2-yl]-methanone;
(102) [5-amino-1-(2-methyl-1H-benzimidazol-5-yl)-1H-pyrazol-4-yl]-(5-pyridin-3-yl-1H-indol-2-yl)-methanone;
(103) [5-amino-1-(2-methyl-1H-benzimidazol-5-yl)-1H-pyrazol-4-yl]-[5-(6-piperazin-1-yl-pyridin-3-yl)-1H-indol-2-yl]-methanone;
(104) [5-amino-1-(2-methyl-1H-benzimidazol-5-yl)-1H-pyrazol-4-yl]-[5-(6-hydroxy-pyridin-3-yl)-1H-indol-2-yl]-methanone;
(105) [5-amino-1-(2-methyl-1H-benzimidazol-5-yl)-1H-pyrazol-4-yl]-[6-fluoro-5-(4-methyl-piperazin-1-ylmethyl)-1H-indol-2-yl]-methanone;
(106) [5-amino-1-(2-methyl-1H-benzimidazol-5-yl)-1H-pyrazol-4-yl]-(6-fluoro-5-pyrrolidin-1- ylmethyl-1H-indol-2-yl)-methanone;
(107) [5-amino-1-(2-methyl-1H-benzimidazol-5-yl)-1H-pyrazol-4-yl]-[6-(1-methyl-piperidin-4-yl)-1H-indol-2-yl]-methanone;
(108) [5-amino-1-(2-methyl-1H-benzimidazol-5-yl)-1H-pyrazol-4-yl]-[6-(4-morpholin-4-yl-phenyl)-1H-indol-2-yl]-methanone;
(109) [5-amino-1-(2-methyl-1H-benzimidazol-5-yl)-1H-pyrazol-4-yl]-[6-(3,4,5,6-tetrahydro-2H-[1,2']bipyridin-5'-yl)-1H-indol-2-yl]-methanone;
(110) [5-amino-1-(2-methyl-1H-benzimidazol-5-yl)-1H-pyrazol-4-yl]-[6-piperazin-1-yl-pyridin-3-yl)-1H-indol-2-yl]-methanone;
(111) [5-amino-1-(2-methyl-1H-benzimidazol-5-yl)-1H-pyrazol-4-yl]-[5-(6-methoxy-pyridin-3-yl)-1H-indol-2-yl]-methanone;
(112) [5-amino-1-(2-methyl-1H-benzimidazol-5-yl)-1H-pyrazol-4-yl]-[5-((S)-3-methyl-morpholin-4-ylmethyl-1H-indol-2-yl]-methanone;
(113) [5-amino-1-(2-methyl-1H-benzimidazol-5-yl)-1H-pyrazol-4-yl]-[4-((R)-3-fluoro-pyrrolidin-1-ylmethyl)-1H-indol-2-yl]-methanone;
(114) [5-amino-1-(2-methyl-1H-benzimidazol-5-yl)-1H-pyrazol-4-yl]-[5-(2,5-dimethyl-pyrrolidin-1-ylmethyl)-1H-indol-2-yl]-methanone;
(115) [5-amino-1-(2-methyl-1H-benzimidazol-5-yl)-1H-pyrazol-4-yl]-[5-(3-fluoro-piperidin-1-ylmethyl)-1H-indol-2-yl]-methanone;
(116) [5-amino-1-(2-methyl-1H-benzimidazol-5-yl)-1H-pyrazol-4-yl]-[5-(3,3-difluoro-piperidin-1-ylmethyl)-1H-indol-2-yl]-methanone;
(117) [5-amino-1-(2-methyl-1H-benzimidazol-5-yl)-1H-pyrazol-4-yl]-{6-[2-(4-methyl-piperazin-1-yl)pyridin-4-yl]-1H-indol-2-yl}-methanone;

(118) [5-amino-1-(2-methyl-1H-benzimidazol-5-yl)-1H-pyrazol-4-yl]-(6-pyridin-4-yl-1H-indol-2-yl)-methanone;
(119) [5-amino-1-(2-methyl-1H-benzimidazol-5-yl)-1H-pyrazol-4-yl]-[5-(4-fluoropiperidin-1-ylmethyl)-1H-indol-2-yl]-methanone;
(120) [5-amino-1-(2-methyl-1H-benzimidazol-5-yl)-1H-pyrazol-4-yl]-[5-(4,4-difluoro-piperidin-1-ylmethyl)-1H-indol-2-yl]-methanone;
(121) [5-amino-1-(2-methyl-1H-benzimidazol-5-yl)-1H-pyrazol-4-yl]-[5-(1-methyl-piperidin-4-yl)-1H-indol-2-yl]-methanone;
(122) [5-amino-1-(2-methyl-1H-benzimidazol-5-yl)-1H-pyrazol-4-yl]-(1H-indol-2-yl)-methanone;
(123) [5-amino-1-(2-methyl-1H-benzimidazol-5-yl)-1H-pyrazol-4-yl]-[5-(3,3-difluoro-pyrrolidin-1-ylmethyl)-1H-indol-2-yl]-methanone;
(124) [5-amino-1-(2-methyl-1H-benzimidazol-5-yl)-1H-pyrazol-4-yl]-[5-(1-cyclopentyl-piperidin-4-yl)-1H-indol-2-yl]-methanone;
(125) [5-amino-1-(2-methyl-1H-benzimidazol-5-yl)-1H-pyrazol-4-yl]-[5-(1-cyclohexyl-piperidin-4-yl)-1H-indol-2-yl]-methanone;
(132) [5-amino-1-(2-methyl-1H-benzimidazol-5-yl)-1H-pyrazol-4-yl]-(6-morpholin-4-ylmethyl-1H-indol-2-yl)-methanone;
(133) [5-amino-1-(2-methyl-1H-benzimidazol-5-yl)-1H-pyrazol-4-yl]-[4-(2-morpholin-4-yl-ethylamino)-1H-indol-2-yl]-methanone;
(134) [5-amino-1-(2-methyl-1H-benzimidazol-5-yl)-1H-pyrazol-4-yl]-[5-(4-methyl-piperazine-1-carbonyl)-1H-indol-2-yl]-methanone;
(135) [5-amino-1-(2-methyl-1H-benzimidazol-5-yl)-1H-pyrazol-4-yl]-[6-(2-morpholin-4-yl-ethylamino)-1H-indol-2-yl]-methanone;
(136) [5-amino-1-(2-methyl-1H-benzimidazol-5-yl)-1H-pyrazol-4-yl]-[5-(piperazine-1-carbonyl)-1H-indol-2-yl]-methanone;
(137) [5-amino-1-(2-methyl-1H-benzimidazol-5-yl)-1H-pyrazol-4-yl]-[4-(2-methoxy-ethylamino)-1H-indol-2-yl]-methanone;
(138) [5-amino-1-(2-methyl-1H-benzimidazol-5-yl)-1H-pyrazol-4-yl]-[4-(2-hydroxy-1-hydroxymethyl-ethylamino)-1H-indol-2-yl]-methanone;
(139) [5-amino-1-(2-methyl-1H-benzimidazol-5-yl)-1H-pyrazol-4-yl]-[4-(2-pyridin-4-yl-ethylamino)-1H-indol-2-yl]-methanone;
(140) [5-amino-1-(2-methyl-1H-benzimidazol-5-yl)-1H-pyrazol-4-yl]-[6-(2-methoxy-ethylamino)-1H-indol-2-yl]-methanone;
(141) [5-amino-1-(2-methyl-1H-benzimidazol-5-yl)-1H-pyrazol-4-yl]-(6-morpholin-4-yl-1H-indol-2-yl)-methanone;
(142) [5-amino-1-(2-methyl-1H-benzimidazol-5-yl)-1H-pyrazol-4-yl]-(4-morpholin-4-yl-1H-indol-2-yl)-methanone;
(143) [5-amino-1-(2-methyl-1H-benzimidazol-5-yl)-1H-pyrazol-4-yl]-(4-morpholin-4-ylmethyl-1H-indol-2-yl)-methanone;
(144) [5-amino-1-(2-methyl-1H-benzimidazol-5-yl)-1H-pyrazol-4-yl]-(5-morpholin-4-ylmethyl-1H-indol-2-yl)-methanone;
(145) [5-amino-1-(2-methyl-1H-benzimidazol-5-yl)-1H-pyrazol-4-yl]-[5-(morpholine-4-carbonyl)-1H-indol-2-yl]-methanone;
(146) [5-amino-1-(2-methyl-1H-benzimidazol-5-yl)-1H-pyrazol-4-yl]-(1H-indol-2-yl)-methanone;
(147) [5-amino-1-(2-methyl-1H-benzimidazol-5-yl)-1H-pyrazol-4-yl]-(1H-indol-2-yl)-methanone;
(148) [5-amino-1-(2-methyl-1H-benzimidazol-5-yl)-1H-pyrazol-4-yl]-(1H-indol-2-yl)-methanone;
(149) [5-amino-1-(2-methyl-1H-benzimidazol-5-yl)-1H-pyrazol-4-yl]-(1H-indol-2-yl)-methanone;
(150) [5-amino-1-(2-methyl-1H-benzimidazol-5-yl)-1H-pyrazol-4-yl]-(1H-indol-2-yl)-methanone;
(151) [5-amino-1-(2-methyl-1H-benzimidazol-5-yl)-1H-pyrazol-4-yl]-(1H-indol-2-yl)-methanone;
(152) 1-(4-{2-[5-amino-1-(2-methyl-1H-benzimidazol-5-yl)-1H-pyrazole-4-carbonyl]-1H-indol-5-ylmethyl}-piperazin-1-yl)-ethanone;
(153) [5-amino-1-(2-methyl-1H-benzimidazol-5-yl)-1H-pyrazol-4-yl]-[5-(4-methanesulfonyl-piperazin-1-ylmethyl)-1H-indol-2-yl]-methanone;
(154) [5-amino-1-(2-methyl-1H-benzimidazol-5-yl)-1H-pyrazol-4-yl]-(5-piperazin-1-ylmethyl-1H-indol-2-yl)-methanone;
(155) 1-(4-{2-[5-amino-1-(2-methyl-1H-benzimidazol-5-yl)-1H-pyrazole-4-carbonyl]-1H-indol-6-ylmethyl}-piperazin-1-yl)-ethanone;
(156) [5-amino-1-(2-methyl-1H-benzimidazol-5-yl)-1H-pyrazol-4-yl]-[6-(4-methyl-piperazin-1-ylmethyl)-1H-indol-2-yl]-methanone;
(157) [5-amino-1-(2-methyl-1H-benzimidazol-5-yl)-1H-pyrazol-4-yl]-[5-(4-methyl-piperazin-1-ylmethyl)-1H-indol-2-yl]-methanone;
(158) [5-amino-1-(2-methyl-1H-benzimidazol-5-yl)-1H-pyrazol-4-yl]-(5-pyrrolidin-1-ylmethyl-1H-indol-2-yl)-methanone;
(159) [5-amino-1-(2-methyl-1H-benzimidazol-5-yl)-1H-pyrazol-4-yl]-(4-fluoro-1H-indol-2-yl)-methanone;
(160) [5-amino-1-(2-methyl-1H-benzimidazol-5-yl)-1H-pyrazol-4-yl]-(5-fluoro-1H-indol-2-yl)-methanon;
(161) [5-amino-1-(2-methyl-1H-benzimidazol-5-yl)-1H-pyrazol-4-yl]-(6-fluoro-1H-indol-2-yl)-methanone;
(163) [5-amino-1-(2-methyl-1H-benzimidazol-5-yl)-1H-pyrazol-4-yl]-(5-fluoro-6-morpholine-4-ylmethyl-1H-indol-2-yl)-methanone;
(164) 2-[5-amino-1-(2-methyl-1H-benzimidazol-5-yl)-1H-pyrazol-4-carbonyl]-1H-indole-5-carboxylic acid;
(165) [5-amino-1-(2-methyl-1H-benzimidazol-5-yl)-1H-pyrazol-4-yl]-(5-methoxy-1H-indol-2-yl)-methanone;
(166) [5-amino-1-(2-methyl-1H-benzimidazol-5-yl)-1H-pyrazol-4-yl]-(4,6-dimethoxy-1H-indol-2-yl)-methanone;
(167) [5-amino-1-(2-methyl-1H-benzimidazol-5-yl)-1H-pyrazol-4-yl]-(4-methoxy-1H-indol-2-yl)-methanone;
(168) [5-amino-1-(2-methyl-1H-benzimidazol-5-yl)-1H-pyrazol-4-yl]-(6-methoxy-1H-indol-2-yl)-methanone;
(169) [5-amino-1-(2-methyl-1H-benzimidazol-5-yl)-1H-pyrazol-4-yl]-(4,6-dimethyl-1H-indol-2-yl)-methanone
(170) [5-amino-1-(2-methyl-1H-benzimidazol-5-yl)-1H-pyrazol-4-yl]-(5-tert-butyl-1H-indol-2-yl)-methanone;
(171) [5-amino-1-(2-methyl-1H-benzimidazol-5-yl)-1H-pyrazol-4-yl]-(5-isopropyl-1H-indol-2-yl)-methanone;
(172) [5-amino-1-(2-methyl-1H-benzimidazol-5-yl)-1H-pyrazol-4-yl]-(5-benzyloxy-1H-indol-2-yl)-methanone;
(173) [5-amino-1-(2-methyl-1H-benzimidazol-5-yl)-1H-pyrazol-4-yl]-(4-benzyloxy-1H-indol-2-yl)-methanone;
(174) [5-amino-1-(2-methyl-1H-benzimidazol-5-yl)-1H-pyrazol-4-yl]-(5,6-dimethoxy-1H-indol-2-yl)-methanone;
(175) [5-amino-1-(2-methyl-1H-benzimidazol-5-yl)-1H-pyrazol-4-yl]-(6-tert-butyl-1H-indol-2-yl)-methanone;

(176) [5-amino-1-(2-methyl-1H-benzimidazol-5-yl)-1H-pyrazol-4-yl]-(5-fluoro-4-trifluoromethyl-1H-indol-2-yl)-methanone;
(177) [5-amino-1-(2-methyl-1H-benzimidazol-5-yl)-1H-pyrazol-4-yl]-(5-phenoxy-1H-indol-2-yl)-methanone;
(178) [5-amino-1-(2-methyl-1H-benzimidazol-5-yl)-1H-pyrazol-4-yl]-(6-methylsulfanyl-1H-indol-2-yl)-methanone;
(179) [5-amino-1-(2-methyl-1H-benzimidazol-5-yl)-1H-pyrazol-4-yl]-(4-tert-butyl-1H-indol-2-yl)-methanone;
(180) [5-amino-1-(2-methyl-1H-benzimidazol-5-yl)-1H-pyrazol-4-yl]-(5-methyl-1H-indol-2-yl)-methanone;
(181) [5-amino-1-(2-methyl-1H-benzimidazol-5-yl)-1H-pyrazol-4-yl]-(5-ethyl-1H-indol-2-yl)-methanone;
(182) [5-amino-1-(2-methyl-1H-benzimidazol-5-yl)-1H-pyrazol-4-yl]-(5-fluoro-6-trifluoromethyl-1H-indol-2-yl)-methanone;
(183) [5-amino-1-(2-methyl-1H-benzimidazol-5-yl)-1H-pyrazol-4-yl]-(6-fluoro-5-methoxy-1H-indol-2-yl)-methanone;
(184) [5-amino-1-(2-methyl-1H-benzimidazol-5-yl)-1H-pyrazol-4-yl]-(6-chloro-5-methoxy-1H-indol-2yl)-methanone;
(185) [5-amino-1-(2-methyl-1H-benzimidazol-5-yl)-1H-pyrazol-4-yl]-(5-chloro-6-methoxy-1H-indol-2-yl)-methanone;
(186) [5-amino-1-(2-methyl-1H-benzimidazol-5-yl)-1H-pyrazol-4-yl]-(6-isopropoxy-1H-indol-2-yl)-methanone;
(187) [5-amino-1-(2-methyl-1H-benzimidazol-5-yl)-1H-pyrazol-4-yl]-(6-benzyloxy-1H-indol-2-yl)-methanone;
(188) [5-amino-1-(2-methyl-1H-benzimidazol-5-yl)-1H-pyrazol-4-yl]-(4-isopropoxy-1H-indol-2-yl)-methanone;
(189) [5-amino-1-(2-methyl-1H-benzimidazol-5-yl)-1H-pyrazol-4-yl]-(2,3-dihydro-6H-[1,4]dioxino[2,3-f]indol-7-yl)-methanone;
(190) [5-amino-1-(2-methyl-1H-benzimidazol-5-yl)-1H-pyrazol-4-yl]-(4,6-di-tert-butyl-1H-indol-2-yl)-methanone;
(191) 2-[5-amino-1-(2-methyl-1H-benzimidazol-5-yl)-1H-pyrazole-4-yl]-1H-indole-4-carbonitrile;
(192) [5-amino-1-(2-methyl-1H-benzimidazol-5-yl)-1H-pyrazol-4-yl]-(5-imidazol-1-yl-1H-indol-2-yl)-methanone;
(193) [5-amino-1-(2-methyl-1H-benzimidazol-5-yl)-1H-pyrazol-4-yl]-(5-trifluoromethylsulfanyl-1H-indol-2-yl)-methanone;
(194) [5-amino-1-(2-methyl-1H-benzimidazol-5-yl)-1H-pyrazol-4-yl]-(5-methylsulfanyl-1H-indol-2-yl)-methanone;
(195) [5-amino-1-(2-methyl-1H-benzimidazol-5-yl)-1H-pyrazol-4-yl]-(5-methanesulfonyl-1H-indol-2-yl)-methanone;
(196) [5-amino-1-(2-methyl-1H-benzimidazol-5-yl)-1H-pyrazol-4-yl]-[6-(4,4-difluoro-piperidin-1-ylmethyl)-1H-indol-2-yl]-methanone;
(197) [5-amino-1-(2-methyl-1H-benzimidazol-5-yl)-1H-pyrazol-4-yl]-[6-(4-fluoro-piperidin-1-ylmethyl)-1H-indol-2-yl]-methanone;
(198) [5-amino-1-(2-methyl-1H-benzimidazol-5-yl)-1H-pyrazol-4-yl]-[6-(oxetan-3-yloxy)-1H-indol-2-yl]-methanone;
(199) [5-amino-1-(2-methyl-1H-benzimidazol-5-yl)-1H-pyrazol-4-yl]-(6-hydroxy-1H-indol-2-yl)-methanone;
(200) [5-amino-1-(2-methyl-1H-benzimidazol-5-yl)-1H-pyrazol-4-yl]-(6-methanesulfonyl-1H-indol-2-yl)-methanone;
(204) [5-amino-1-(2-methyl-1H-benzimidazol-5-yl)-1H-pyrazol-4-yl]-(6-chloro-1H-indol-2-yl)-methanone;
(205) [5-amino-1-(2-methyl-1H-benzimidazol-5-yl)-1H-pyrazol-4-yl]-(5-chloro-1H-indol-2-yl)-methanone;
(206) [5-amino-1-(2-methyl-1H-benzimidazol-5-yl)-1H-pyrazol-4-yl]-(1H-indol-3-yl)-methanone;
(207) [5-amino-1-(2-methyl-1H-benzimidazol-5-yl)-1H-pyrazol-4-yl]-(1H-indol-6-yl)-methanone;
(208) [5-amino-1-(2-methyl-1H-benzimidazol-5-yl)-1H-pyrazol-4-yl]-(5-bromo-6-fluoro-1H-indol-2-yl)-methanone;
(209) [5-amino-1-(2-methyl-1H-benzimidazol-5-yl)-1H-pyrazol-4-yl]-(5-bromo-6-fluoro-1H-indol-2-yl)-methanone;
(210) [5-amino-1-(2-methyl-1H-benzimidazol-5-yl)-1H-pyrazol-4-yl]-(5-trifluoromethyl-1H-indol-2-yl)-methanone;
(211) [5-amino-1-(2-methyl-1H-benzimidazol-5-yl)-1H-pyrazol-4-yl]-(5-trifluoromethoxy-1H-indol-2-yl)-methanone;
(212) [5-amino-1-(2-methyl-1H-benzimidazol-5-yl)-1H-pyrazol-4-yl]-(4,6-dichloro-1H-indol-2-yl)-methanone;
(213) [5-amino-1-(2-methyl-1H-benzimidazol-5-yl)-1H-pyrazol-4-yl]-(6-bromo-4-fluoro-1H-indol-2-yl)-methanone;
(214) [5-amino-1-(2-methyl-1H-benzimidazol-5-yl)-1H-pyrazol-4-yl]-(6-trifluoromethoxy-1H-indol-2-yl)-methanone;
(215) [5-amino-1-(2-methyl-1H-benzimidazol-5-yl)-1H-pyrazol-4-yl]-(5-trifluoromethoxy-1H-indol-2-yl)-methanone;
(216) [5-amino-1-(2-methyl-1H-benzimidazol-5-yl)-1H-pyrazol-4-yl]-(5-trifluoromethyl-1H-indol-2-yl)-methanone;
(217) [5-amino-1-(2-methyl-1H-benzimidazol-5-yl)-1H-pyrazol-4-yl]-(5,6-dichloro-1H-indol-2-yl)-methanone;
(218) [5-amino-1-(2-methyl-1H-benzimidazol-5-yl)-1H-pyrazol-4-yl]-(6-bromo-5-fluoro-1H-indol-2-yl)-methanone;
(219) [5-amino-1-(2-methyl-1H-benzimidazol-5-yl)-1H-pyrazol-4-yl]-(4,5-dichloro-1H-indol-2-yl)-methanone;
(220) [5-amino-1-(2-methyl-1H-benzimidazol-5-yl)-1H-pyrazol-4-yl]-(4,6-difluoro-1H-indol-2-yl)-methanone;
(221) [5-amino-1-(2-methyl-1H-benzimidazol-5-yl)-1H-pyrazol-4-yl]-[6-(3-chloro-pyridin-4-yl)-1H-indol-2-yl]-methanone;
(222) [5-amino-1-(2-methyl-1H-benzimidazol-5-yl)-1H-pyrazol-4-yl]-[6-(6-methyl-pyridine-3-yl)-1H-indol-2-yl]-methanone;
(223) [5-amino-1-(2-methyl-1H-benzimidazol-5-yl)-1H-pyrazol-4-yl]-[6-(5-fluoro-pyridine-3-yl)-1H-indol-2-yl]-methanone;
(224) [5-amino-1-(2-methyl-1H-benzimidazol-5-yl)-1H-pyrazol-4-yl]-[6-(2-trifluoromethyl-pyridin-3-yl)-1H-indol-2-yl]-methanone;
(225) [5-amino-1-(2-methyl-1H-benzimidazol-5-yl)-1H-pyrazol-4-yl]-[6-(5-chloro-2-methoxy-pyridin-3-yl)-1H-indol-2-yl]-methanone;
(226) [5-amino-1-(2-methyl-1H-benzimidazol-5-yl)-1H-pyrazol-4-yl]-[6-(5-chloro-pyridin-3-yl)-1H-indol-2-yl]-methanone;
(227) [5-amino-1-(2-methyl-1H-benzimidazol-5-yl)-1H-pyrazol-4-yl]-(6-thiophen-3-yl-1H-indol-2-yl)-methanone;
(228) [5-amino-1-(2-methyl-1H-benzimidazol-5-yl)-1H-pyrazol-4-yl]-[6-(4-chloropyridin-3-yl)-1H-indol-2-yl]-methanone;

(229) [5-amino-1-(2-methyl-1H-benzimidazol-5-yl)-1H-pyrazol-4-yl]-(6-thiophen-2-yl-1H-indol-2-yl)-methanone;
(230) [5-amino-1-(2-methyl-1H-benzimidazol-5-yl)-1H-pyrazol-4-yl]-[6-(3-fluoro-pyridin-4-yl)-1H-indol-2-yl]-methanone;
(231) [5-amino-1-(2-methyl-1H-benzimidazol-5-yl)-1H-pyrazol-4-yl]-[6-(2-trifluoromethyl-pyridin-4-yl)-1H-indol-2-yl]-methanone;
(232) [5-amino-1-(2-methyl-1H-benzimidazol-5-yl)-1H-pyrazol-4-yl]-[5-(3,3-difluoro-pyrrolidine-1-carbonyl)-1H-indol-2-yl]-methanone;
(233) [5-amino-1-(2-methyl-1H-benzimidazol-5-yl)-1H-pyrazol-4-yl]-[5-(2,6-dimethyl-morpholine-4-carbonyl)-1H-indol-2-yl]-methanone;
(234) [5-amino-1-(2-methyl-1H-benzimidazol-5-yl)-1H-pyrazol-4-yl]-[5-([1,4']bipiperidinyl-1'-carbonyl)-1H-indol-2-yl]-methanone;
(235) [5-amino-1-(2-methyl-1H-benzimidazol-5-yl)-1H-pyrazol-4-yl]-{5-[4-(2,2,2-trifluoro-ethyl)-piperazine-1-carbonyl]-1H-indol-2-yl}-methanone;
(236) [5-amino-1-(2-methyl-1H-benzimidazol-5-yl)-1H-pyrazol-4-yl]-{5-[4-(2-hydroxy-ethyl)-piperazine-1-carbonyl]-1H-indol-2-yl}-methanone;
(237) [5-amino-1-(2-methyl-1H-benzimidazol-5-yl)-1H-pyrazol-4-yl]-[5-(3,3,4,4-tetrafluoro-pyrrolidine-1-carbonyl)-1H-indol-2-yl]-methanone;
(238) [5-amino-1-(2-methyl-1H-benzimidazol-5-yl)-1H-pyrazol-4-yl]-[5-((R)-3-fluoro-pyrrolidine-1-carbonyl)-1H-indol-2-yl]-methanone; and
(239) [5-amino-1-(2-methyl-1H-benzimidazol-5-yl)-1H-pyrazol-4-yl]-[5-((S)-3-fluoro-pyrrolidine-1-carbonyl)-1H-indol-2-yl]-methanone.

Of them, (1) [5-amino-1-(2-methyl-1H-benzimidazol-5-yl)-1H-pyrazol-4-yl]-(1H-indol-2-yl)-methanone or a tautomer thereof is preferred.

The compound is particularly preferably the following compound or a tautomer thereof (hereinafter, the following compound is called "Compound 1").

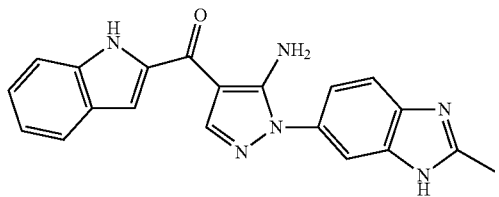 [SMILES: Cc1nc2ccc(-n3ncc(C(=O)c4cc5ccccc5[nH]4)c3N)cc2[nH]1]

Such compounds applied to the present invention are known as described in Patent Document 1 (WO 2011/16528), and can be prepared by the methods described in Patent Document 1.

Various isomers geometric isomers, optical isomers based on asymmetric carbons, rotamers, stereoisomers, and tautomers) of the compounds applied to the present invention can be purified and isolated using common separation means, for example, recrystallization, diastereomeric salt formation, enzymatic resolution, and various chromatography methods (e.g., thin-layer chromatography, column chromatography, high performance liquid chromatography, and gas chromatography).

When the compounds applied in the present invention are obtained as free forms, they can be converted to salts that may be formed by the compounds or hydrates thereof according to conventional methods. If the compounds according to the present invention are obtained as salts or hydrates of the compounds, they can be converted to free forms of the compounds according to conventional methods.

As described in Patent Document 1 (WO 2011/16528), the compounds applied in the present invention are useful as compounds having an effect of inhibiting fibroblast growth factor receptor (FGFR) family kinases. They are useful for the prevention and/or treatment of cancer such as breast cancer, acute myeloid leukemia, pancreatic cancer, bladder cancer, prostatic cancer, esophageal cancer, angiogenesis, gastric cancer, endometrial cancer, ovarian cancer, brain tumor (including glioblastoma), colon cancer, multiple myeloma, hepatoma, lung cancer (including small cell lung cancer and non-small-cell lung cancer), and thyroid cancer.

Alkyl Sulfate Salts

Herein, "alkyl sulfate salts" are salts of alkyl-$OSO_2OH$,
The alkyl is preferably $C_{10-14}$ (linear) alkyl, and more preferably $C_{12}$ alkyl.

The salts preferably include, for example, the inorganic base salts defined above. Preferred examples of the inorganic base salts include alkali metal salts such as sodium salts and potassium salts, alkaline earth metal salts such as calcium salts and magnesium salts, aluminum salts, and ammonium salts. Preferred examples of organic base salts include diethylamine salts, diethanolamine salts, ineglumine salts, and N,N-dibenzylethylenediamine salts.

Of the above salts, sodium salts are preferred.

The "alkyl sulfate salt" is more preferably a lauryl sulfate salt, and particularly preferably sodium lauryl sulfate.

The pharmaceutical formulations according to the present invention contain alkyl sulfate salts. Therefore, when the compounds represented by formula (I) or tautomers thereof, or salts thereof are formulated, gelation of the compounds contained in the formulations can be prevented and suppressed if the formulations are dissolved in water or the like, and the dissolution properties can be improved.

In this case, the ratio by weight between the compound represented by formula (I) or a tautomer thereof, or a pharmaceutically acceptable salt thereof and the alkyl sulfate salt in a pharmaceutical formulation according to the present invention is preferably 1:10 to 8:1, more preferably 1:2 to 8:1, still more preferably 1:1 to 5:1, yet more preferably 1:1 to 3:1, and even more preferably 2:1, in terms of the free form of the compound represented by formula (I) or a tautomer thereof, or a pharmaceutically acceptable salt thereof.

The ratio by weight between Compound I or a tautomer thereof or a pharmaceutically acceptable salt (preferably, malate) thereof and sodium lauryl sulfate in a pharmaceutical formulation according to the present invention is preferably 1:10 to 8:1, more preferably 1:2 to 8:1, still more preferably 1:1 to 5:1, yet more preferably 1:1 to 3:1, and even more preferably 2:1, in terms of the free form of Compound 1 described above or a tautomer thereof, or a pharmaceutically acceptable salt (preferably, a malate) thereof.

Accordingly, the alkyl sulfate salts are extremely useful for anti-gelation agents for pharmaceutical formulations, in particular, solid pharmaceutical formulations, containing the compounds represented by formula (I) or tautomers thereof, or pharmaceutically acceptable salts thereof.

Pharmaceutical Formulations

The pharmaceutical formulations according to the present invention contain compounds represented by general formula (I) or tautomers thereof, or pharmaceutically acceptable salts thereof, and alkyl sulfate salts.

Such pharmaceutical formulations are preferably solid formulations. Solid formulations can be prepared as tablets, powders, fine granules, granules, coated tablets, capsules, dry syrups, troches, suppositories, and the like.

Of them, the pharmaceutical formulations according to the present invention are preferably capsules, tablets, granules, or dry syrups, and more preferably. capsules or tablets. Such formulations may contain ingredients, range of shapes, sizes, hardness and the like that are commonly used in the field of formulation. The forms and the like of the formulations are not particularly limited.

For example, Capsules No. 5 to No. 00/gelatin of the Japanese Pharmacopoeia which are commonly used in capsule formulation can be used as capsules.

Commonly used tablets such as those having a diameter of 5 mm to 15 mm, a thickness of 3 mm to 5 mm, and a hardness of 60 N (Newton) to 100 N can be used as tablets.

The compounds applied in the present invention which are contained in such pharmaceutical formulations are preferably particles. The particles have an average particle size of preferably 10 μm or less, and more preferably 1 μm to 10 μm.

The pharmaceutical formulations according to the present invention contain the alkyl sulfate salts and the compounds represented by general formula (I) or tautomers thereof, or pharmaceutically acceptable salts thereof Preferably, the pharmaceutical formulations further contain disintegrants.

Examples of the disintegrants include croscarmellose sodium, carmellose calcium, crospovidone, sodium carboxymethyl starch, low-substituted hydroxypropylcellulose, corn starch, and soybean polysaccharide.

Further, of the disintegrants of the present invention, disintegrants known as "super disintegrants" which are swelling disintegrants having a swelling rate of 200% or more are preferable.

Examples of the super disintegrants include croscarmellose sodium, crospovidone, carmellose calcium, sodium carboxymethyl starch, and soybean polysaccharide. Croscarmellose sodium is preferred.

When the pharmaceutical formulation according to the present invention is a capsule, the ratio by weight between the compound represented by formula (I) or a tautomer thereof, or a pharmaceutically acceptable salt thereof and the alkyl sulfate salt is preferably 1:10 to 8:1, more preferably 1:2 to 8:1, still more preferably 1:1 to 5:1, yet more preferably 1:1 to 3:1, and even more preferably 2:1, in terms of the free form of the compound represented by formula (I) or a tautomer thereof, or a pharmaceutically acceptable salt thereof.

When the pharmaceutical formulation according to the present invention is a capsule, the ratio by weight between Compound 1 described above or a tautomer thereof, or a pharmaceutically acceptable salt (preferably, a malate) thereof and sodium lauryl sulfate is preferably 1:10 to 8:1, more preferably 1:2 to 8:1, still more preferably 1:1 to 5:1, yet more preferably 1:1 to 3:1, and even more preferably 2:1, in terms of the free form of Compound 1 described above or a tautomer thereof, or a pharmaceutically acceptable salt (preferably a malate) thereof.

The alkyl sulfate salt may be added to the capsule of the present invention at 0.5% to 10% by weight, preferably 1% to 5% by weight, and particularly preferably 4% to 5% by weight.

Sodium lauryl sulfate, which is a preferred alkyl sulfate salt, may be added to the capsule of the present invention at 0.5% to 10% by weight, preferably 1% to 5% by weight, and particularly preferably 4% to 5% by weight.

One capsule contains the compound represented by formula (I) or a tautomer thereof, or a pharmaceutically acceptable salt thereof at a content ratio of preferably 10% by weight or less, more preferably 0.1% to 10% by weight, still more preferably 0.5% to 10% by weight, and particularly preferably 0.5% to 8% by weight, in terms of free form, to the total amount of the pharmaceutical formulation, excluding the weight of the capsule shell (hereinafter, the same applies to the total amount of a pharmaceutical formulation when the pharmaceutical formulation is a capsule).

The content ratio of Compound 1 or a tautomer thereof, or a pharmaceutically acceptable salt (preferably, a malate) thereof is preferably 10% by weight or less, more preferably 0.1% to 10% by weight, still more preferably 0.5% to 10% by weight, and particularly preferably 0.5% to 8% by weight, in terms of free form, to the total amount of the pharmaceutical formulation, excluding the weight of the capsule shell (hereinafter, the same applies to the total amount of a pharmaceutical formulation when the pharmaceutical formulation is a capsule).

When the pharmaceutical formulation according to the present invention is a capsule, the content of the compound represented by formula (I) or a tautomer thereof, or a pharmaceutically acceptable salt thereof, relative to the total amount of the capsule, is preferably 1 mg to 500 mg, more preferably 10 mg to 200 mg, and still more preferably 20 mg to 100 mg, in terms of free form, per capsule.

When the pharmaceutical formulation according to the present invention is a capsule, the content of Compound 1 described above or a. tautomer thereof, or a pharmaceutically acceptable salt (preferably, a malate) thereof, relative to the total amount of the capsule, is preferably 1 mg to 500 mg, more preferably 10 mg to 200 mg, and still more preferably 20 mg to 100 mg, in terms of free form, per capsule.

When the content of the compound represented by formula (I) or a tautomer thereof, or a pharmaceutically acceptable salt thereof in such a capsule is 20 mg or more in terms of free form, its concentration is particularly preferably 10% by weight or less.

When the content of Compound 1 or a tautomer thereof, or a pharmaceutically, acceptable salt (preferably, a malate) thereof in such a capsule is 20 mg or more in terms of free form, its concentration is particularly preferably 10% by weight or less.

The super disintegrant such as croscarnellose sodium may be added to the capsule of the present invention at 1% to 10% by weight, preferably 2% to 8% by weight, and particularly preferably 4% to 6% by weight to the total amount of the capsule.

If the content ratio of the compound represented by formula (I) or a tautomer thereof, or a pharmaceutically acceptable salt thereof in the capsule is within such a range, gelation of the above compound can be suppressed and excellent dissolution properties can be provided when it is administered.

When the pharmaceutical formulation according to the present invention is a tablet, the content of the compound represented by formula (I) or a tautomer thereof, or a pharmaceutically acceptable salt thereof, relative to the total amount of the tablet, is preferably 1 mg to 500 mg, more preferably 10 mg to 200 mg, and still more preferably 50 mg to 100 mg, in terms of free form, per tablet.

When the pharmaceutical formulation according to the present invention is a tablet,the content of Compound 1 described above or a tautomer thereof, or a pharmaceutically acceptable salt (preferably, a malate) thereof, relative to the total amount of the tablet, is preferably 1 mg to 500 mg, more preferably 10 mg to 200 mg, and still more preferably 50 mg to 100 mg, in terms of free form, per tablet.

When the content ratio of the compound represented by formula (I) or a tautomer thereof, or a pharmaceutically acceptable salt thereof in the pharmaceutical formulation according to the present invention is high, for example, when it is 10% by weight or more in terms of free form to the total amount of the pharmaceutical formulation, the pharmaceutical formulation is preferably prepared as a tablet.

If the pharmaceutical formulation according to the present invention is a tablet, when the content ratio of Compound 1 described above or a tautomer thereof, or a pharmaceutically acceptable salt (preferably, a malate) thereof in the formulation is high, for example, when it is 1 0% by weight or more in terms of free form to the total amount of the pharmaceutical formulation, the pharmaceutical formulation is preferably prepared as a tablet.

When a pharmaceutical formulation containing the compound applied to the present invention at 10% by weight or more in total is prepared as a tablet, the pharmaceutical formulation has improved disintegration properties as compared with a capsule, and thus the dissolution properties can be further enhanced.

The content ratio of the compound represented by formula (I) or a tautomer thereof, or a pharmaceutically acceptable salt thereof to the total amount of the tablet is preferably 1% to 50% by weight, and more preferably 1% to 40% by weight in terms of free form, per tablet.

The content ratio of Compound 1 described above or a tautomer thereof, or a pharmaceutically acceptable salt (preferably, a malate) thereof to the total amount of the tablet is preferably 1% to 50% by weight, and more preferably 1% to 40% by weight in terms of free form, per tablet.

When the pharmaceutical formulation is a tablet, the ratio by weight between the compound represented by formula (I) or a tautomer thereof, or a pharmaceutically acceptable salt thereof and the alkyl sulfate salt is preferably 1:10 to 8:1, more preferably 1:2 to 8:1, still more preferably 1:1 to 5:1, yet more preferably 1:1 to 3:1, and even more preferably 2:1, in terms of the free form of the compound represented by formula (I) or a tautomer thereof, or a pharmaceutically acceptable salt thereof.

When the pharmaceutical formulation is a tablet, the ratio by weight between Compound 1 described above or a tautomer thereof, or a pharmaceutically acceptable salt (preferably, a malate) thereof and sodium lauryl sulfate is preferably 1:10 to 8:1, more preferably 1:2 to 8:1, still more preferably 1:1 to 5:1, yet more preferably 1:1 to 3:1, and even more preferably 2:1, in terms of the free form of Compound 1 described above or a tautomer thereof, or a pharmaceutically acceptable salt (preferably, a malate) thereof.

The alkyl sulfate salt may be added to the tablet of the present invention at 4% to 40% by weight, preferably 5% to 20% by weight, and particularly preferably 10% to 20% by weight.

Sodium lauryl sulfate, which is a preferred alkyl sulfate salt, can be added to the tablet of the present invention at 4% to 40% by weight, preferably 5% to 20% by weight, and particularly preferably 10% to 20% by weight.

In the present invention, when a disintegrant is added and the dosage form is a tablet, as compared with a capsule, the use of a super disintegrant rather than a normal disintegrant is particularly preferred, because this improves the disintegration properties of the pharmaccu formulation, and thus further enhances dissolution properties.

A super disintegrant such as croscarmellose sodium may be added to the tablet of the present invention at 1% to 10% by weight, preferably 2% to 8% by weight, and particularly preferably 4% to 6% by weight to the total amount of the tablet.

The pharmaceutical formulations according to the present invention can contain, in addition to the above ingredients, commonly used carriers, for example, additives such as excipients, binders, lubricants, colorants, flavoring agents, and as necessary, stabilizers, emulsifiers, absorption promoters, surfactants, pH adjusters, preservatives, and antioxidants. They can be compounded with ingredients commonly used as materials of pharmaceutical formulations, and formulated.

The content of the carrier(s) in the pharmaceutical formulation according to the present invention can be the balance obtained by subtracting the total content of the compound applied in the present invention, the alkyl sulfate salt, and the disintegrant contained as necessary, from the total amount of the pharmaceutical formulation.

The content ratio of the carrier(s) depends on the form of formulation. For example, in the case of a capsule, the content ratio of the carrier(s) to the total amount of the capsule is preferably 0.1% to 99.4% by weight, and preferably 0.1% to 98.4% by weight, when the capsule contains a disintegrant.

In the case of a tablet, the content ratio of the carrier(s) to the total amount of the tablet is preferably 0.1% to 95% by weight per tablet, and preferably 0.1% to 94% by weight when the tablet contains a super disintegrant.

For example, oral formulations are manufactured by adding the compounds according to the present invention or pharmacologically acceptable salts thereof, alkyl sulfate salts, and as necessary, disintegrants, and carriers such as excipients, and if needed, binders, lubricants, colorants, and flavoring agents; and then formulating them into powders, fine granules, granules, tablets, coated tablets, capsules, and the like by conventional methods.

The ingredients include, for example, animal and vegetable oils such as soybean oils, beef tallow, and synthetic glycerides; hydrocarbons such as liquid paraffin, squalane, and solid paraffin; ester oils such as octyldodecyl myristate and isopropyl myristate; higher alcohols such cetostearyl alcohol and biphenyl alcohol; silicon resins; silicon oils; surfactants such as polyoxyethylene fatty acid esters, sorbitan fatty acid esters, glycerin fatty acid esters, polyoxyethylene sorbitan fatty acid esters, polyoxyethylene hydrogenated castor oils, and polyoxyethylene/polyoxypropylene block copolymers; water-soluble polymers such as hydroxyethyl cellulose, polyacrylic acids, carboxyvinyl polymers, polyethylene glycol, polyvinylpyrrolidone, and methyl cellulose; lower alcohols such as ethanol and isopropanol; polyalcohols such as glycerin, propylene glycol, dipropylene glycol, and sorbitol; saccharides such as glucose and sucrose; inorganic powders such as silicic anhydride, magnesium aluminum silicate, and aluminum silicate; and purified water.

Excipients include, for example, lactose, sucrose, glucose, mannitol, sorbit, crystalline cellulose, and silicon dioxide.

Binders include, for example, polyvinyl alcohol, polyvinyl ether, methyl cellulose, ethyl cellulose, Arabic gum, tragacanth, gelatin, shellac, hydroxypropyl methyl cellulose, hydroxypropyl cellulose, polyvinylpyrrolidone, polypropylene glycol/polyoxyethylene block polymer, and meglumine.

Lubricants include, for example, magnesium stearate, talc, polyethylene glycol, silica, and hardened vegetable oil.

Colorants approved for use as additives for pharmaceuticals are used, Flavoring agents used include, for example, cacao powder, menthol, aromatic powder, peppermint oil, borneol, and cinnamon powder.

Of course, these tablets and granules may be coated with sugar, or if needed, other appropriate coatings. Alternatively, when liquid preparations such as syrups and injections are produced, the compounds of the present invention or pharmaceutically acceptable salts thereof are combined with pH adjusting agents, solubilizers, isotonizing agents, or such, and if needed, solubilizing agents, stabilizers, and such, and then formulated.

The dosage of the pharmaceutical formulation according to the present invention can be appropriately selected depending on the severity of symptoms, age, sex, body weight, mode of administration, type of salt, specific type of disease, and the like.

Although the dosage significantly varies depending on the type of disease and severity of symptoms, age, sex, sensitivity to the drug, and such of the patient, the formulation is usually administered to an adult once or several times a day at a daily dosage of about 0.03 to 1000 mg, preferably 0.1 to 500 mg, and more preferably 0.1 to 100 mg.

Methods for Manufacturing Pharmaceutical Formulations

The methods for manufacturing pharmaceutical formulations according to the present invention comprise the steps of:

providing a mixture comprising an alkyl sulfate salt and the above compound applied to the present invention;

granulating the mixture without adding water to the mixture, or by adding an amount of purified water to the mixture at 25% by weight or less to a total amount of the mixture; and providing a dry powder by drying the granulated mixture.

The compound applied to the present invention is preferably prepared as particles in advance, and then subjected to mixing.

Particles of the compound can be prepared by a conventional method. For example, they can be obtained by high pressure spray grinding such as jet milling.

In the step of providing a mixture, the mixture comprising an alkyl sulfate salt and the compound applied to the present invention is more preferably obtained by placing components of the alkyl sulfate salt and the compound applied to the present invention, and as necessary, the above-mentioned ingredients commonly used as materials for pharmaceuticals, into a known mixer granulator or the like, and mixing them.

The mixing temperature and the mixing time are not particularly limited as long as the ingredients are not adversely affected, and are preferably, for example, 0° C. to 50° C. and about 5 to 15 minutes.

In the step of granulating a mixture, one can use methods of granulating the mixture without adding water to the mixture, or methods of granulating the mixture by adding an amount of purified water to the mixture at 25% by weight or less to the total amount of the mixture.

Examples of the methods of granulating the mixture without adding water include dry granulation. Dry granulation is a method by which the mixture is granulated by applying high stress (pressure) without adding water. Representative examples of dry granulation include the granulation method by compression molding of a mixed powder using a roller compactor. The compression molding pressure in this case is preferably 5 kN/cm to 9 kN/cm, and more preferably 6 kN/cm to 8 kN/cm.

Examples of the methods of granulating the mixture by adding water include wet granulation. Wet granulation is a method by which purified water is added to the mixture preferably with stirring to granulate the mixture.

Purified water is added at a content ratio of 25% by weight or less, preferably 15% to 25% by weight, more preferably 18% to 23% by weight, and still more preferably 20% to 22% by weight to the total amount of the mixture.

The stress applied during granulation by a granulation method varies depending on the conditions (for example, in the case of stirring granulation, the stress is higher as the rotational speed of the blade is increased; and the stress varies depending on the instrument). As commonly known, the amount of water required is larger as the stress is higher, and it is smaller as the stress is lower. Therefore, there is no limitation on the amount of water.

The temperature and the time of the granulation step vary depending on the stirring conditions, and are within a range where the ingredients are not adversely affected. They are not particularly limited, and are preferably, for example, 0° C. to 50° C. and about 3 to 5 minutes.

In the step of providing a dry powder, the mixture obtained by granulation can be dried according to a conventional method such as vacuum drying to provide a dry powder.

The drying temperature and the drying time are not particularly limited as long as the ingredients are not adversely affected, and are preferably, for example, 50° C. to 80° C. and about 30 minutes to 2 hours.

The methods for manufacturing a pharmaceutical formulation according to the present invention may further comprise the steps of:

providing a particle size-granulated powder by subjecting the dry powder to particle size granulation;

providing a compounded powder by mixing the particle size-granulated powder and an additive comprising magnesium stearate; and preparing the pharmaceutical formulation in the form of a tablet by tableting the compounded powder.

In the step of providing a particle size-granulated powder by subjecting the dry powder to particle size granulation, the particle size granulation methods are not particularly limited, and conventional methods using a sieve, a sieving machine, or the like can be used.

The particle size-granulated powder can be mixed with a further additive such as magnesium stearate, talc, or stearic acid as necessary, to obtain a compounded powder.

The mixing temperature and the mixing time are not particularly limited as long as the ingredients are not adversely affected, and are preferably, for example, 0° C. to 50° C. and about 3 to 5 minutes.

The compounded powder can be filled into a capsule shell to provide a capsule.

Further, the compounded powder can be tableted by a conventional method to provide a tablet.

All prior art documents cited herein are incorporated into this specification by reference.

EXAMPLES

The present invention will be described in more detail with reference to Examples and Test Examples below, but it is not to be construed as being limited thereto. All starting materials and reagents were obtained from commercial suppliers or synthesized by known methods.

Capsules used in the Examples below were commonly used encapsulated formulations (Capsules No. 2, gelatin of the Japanese Pharmacopoeia).

Tablets were prepared in commonly used tablet forms (diameter: 9 mm, thickness: 3.5 mm to 4.5 mm, hardness: 60 N (newton) to 100 N).

1. Manufacture of Compound 1

A malate of Compound 1 ([5-amino-1-(2-methyl-3H-benzimidazol-5-yl)-1H-pyrazol-4-yl]-(1H-indol-2-yl)-methanone below) was manufactured according to the known method described in Example 1A or the like described in WO 2011/16528.

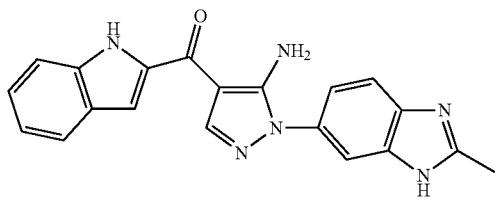 [SMILES: Cc1nc2ccc(-n3ncc(C(=O)c4cc5ccccc5[nH]4)c3N)cc2[nH]1]

Example 1A

Synthesis of [5-amino-1-(2-methyl-3H-benzimidazol-5-yl)-1H-pyrazol-4-yl]-(1H-indol-2-yl)-methanone L-malate

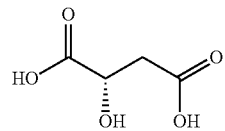

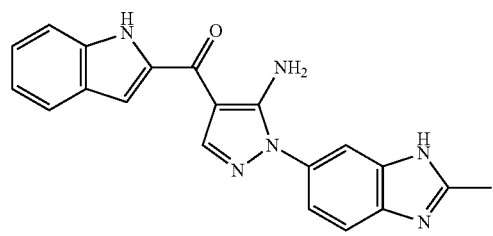

[5-amino-1-(2-methyl-1H-benzimidazol-5-yl)-1H-pyrazol-4-yl]-(1H-indol-2-yl)-methanone hydrate (190 g, 0.507 mol) and L-malic acid (68 g, 0.507 mol) were weighed and dissolved in dimethyl sulfoxide (0.418 L, 2.2 v/w) and acetone (0.418 L, 2.2 v/w), and the reaction solution was then filtered through a Kiriyama funnel (No. 4 filter paper), placed into a 10 L jacketed separable flask, and heated at 50° C.

L-Malic acid (544.4 g, 4.06 mol) was weighed and dissolved in acetone (1.25 L, 6.6 v/w) and acetic acid (0.418 L, 2.2 v/w), and the solution was filtered through the Kiriyama funnel (No. 4 filter paper), and placed into the 10 L jacketed separable flask while not allowing the internal temperature to fall below 45° C. The seed crystals (0.95 g, 0.5%) were suspended in acetone (7.5 mL), and the suspension was placed into the 10 L jacketed separable flask.

After seven hours, the suspension was cooled to 25° C., and the crystals were filtered off through the Kiriyama funnel. The crystals were then washed with acetone (0.85 L, 5 v/w) twice, and the moist powder was placed into the 10 L jacketed separable flask. Acetone (2.85 L, 15 v/w) was placed thereinto, and the suspension was stirred at 50° C. for three hours. The crystals were filtered through the Kiriyama funnel and then washed with acetone (0.85 L, 5 v/w) twice. The moist powder was dried under reduced pressure at an external temperature of 40° C. for three hours to provide [5-amino-1-(2-methyl-3H-benzimidazol-5-yl)-1H-pyrazol-4-yl]-(1H-indol-2-yl)-methanone L-malate (556.9 g, 73%).

$^1$H-NMR (DMSO-D$_6$) δ: 11.69 (1H, s), 8.31 (1H, s), 8.25-7.00 (10H, m), 4.25-4.22 (1H, m), 3.33 (2H, brs), 2.69-2.32 (9H, m)

FAB positive mode m/z 157.1, 232.1, 289,2, 357.2 [(M+H)$^+$]

2. Usefulness of Sodium Lauryl Sulfate (SLS) as Compared with other Surfactants (Manufacture of Pharmaceutical Formulations)

The ingredients listed in Table 1 (excluding magnesium stearate) were put in a mortar and premixed. To this mixture was added 20% by weight (relative to the mixture) of purified water and the mixture was stirred, granulated, and then dried to provide dry powder.

The dry powder was subjected to particle size granulation by a sieve, and the size-granulated powder was mixed with magnesium stearate in the mortar to provide a compounded powder.

The compounded powder was filled into a capsule shell to manufacture a capsule.

TABLE 1

| | Content per capsule (mg) | | | | | |
|---|---|---|---|---|---|---|
| | Example 1 | Comparative Example 1 | Comparative Example 2 | Comparative Example 3 | Comparative Example 4 | Comparative Example 5 |
| Compound 1 malate bulk drug (as free form) | 27.5 (20) | 27.5 (20) | 27.5 (20) | 27.5 (20) | 27.5 (20) | 27.5 (20) |
| Lactose hydrate | 111.5 | 111.5 | 111.5 | 111.5 | 111.5 | 111.5 |
| Crystalline cellulose | 30.0 | 30.0 | 30.0 | 30.0 | 30.0 | 30.0 |
| Croscarmellose Na | 10.0 | 10.0 | 10.0 | 10.0 | 10.0 | 10.0 |
| Hydroxypropylcellulose | 10.0 | 10.0 | 10.0 | 10.0 | 10.0 | 10.0 |
| Sodium lauryl sulfate | 10.0 | | | | | |
| Polysorbate 80 | | 10.0 | | | | |
| Polyoxyl 40 stearate | | | 10.0 | | | |
| Polyoxyethylene hydrogenated castor oil 60 | | | | 10.0 | | |

TABLE 1-continued

| | Content per capsule (mg) | | | | | |
|---|---|---|---|---|---|---|
| | Example 1 | Comparative Example 1 | Comparative Example 2 | Comparative Example 3 | Comparative Example 4 | Comparative Example 5 |
| Lauromacrogol | | | | | 10.0 | |
| Polyoxyethylene (10) octylphenyl ether | | | | | | 10.0 |
| Magnesium stearate | 1.0 | 1.0 | 1.0 | 1.0 | 1.0 | 1.0 |
| Total | 200 | 200 | 200 | 200 | 200 | 200 |

(Evaluation of Formulations)

The disintegration properties of Example 1 and Comparative Examples 1 to 5 in a dissolution tester were visually observed using Dissolution Test Solution 1 of the Japanese Pharmacopoeia. The results are shown in Table 2 . Dissolution properties of formulations (such as capsules and tablets) serve to evaluate absorption properties of pharmaceuticals contained in the formulations. Evaluation of disintegration properties is brief evaluation of dissolution properties, because the formulations are disintegrated and then dissolved in aqueous solutions.

TABLE 2

| | Content per capsule (mg) | | | | | |
|---|---|---|---|---|---|---|
| | Example 1 | Comparative Example 1 | Comparative Example 2 | Comparative Example 3 | Comparative Example 4 | Comparative Example 5 |
| Disintegration properties in Dissolution Test Solution 1 of the Japanese Pharmacopoeia | ○ | x | x | x | x | x |

○: disintegrated within 60 minutes
x: not disintegrated within 60 minutes (Effect of Surfactants)

The surfactants shown in Table 3 and Dissolution Test Solution 1 of the Japanese Pharmacopoeia were used, and the concentration of each surfactant was adjusted to 5%. Compound 1 malate was sufficiently added thereto, the mixture was stirred, and the solubility after 24 hours was measured.

TABLE 3

| Surfactant | Solubility of Compound 1 (μg/mL) |
|---|---|
| (None) | 18.51 |
| Sodium lauryl sulfate | 136.43 |
| Polysorbate 80 | 138.16 |
| Polyoxyethylene (10) octylphenyl ether | 144.66 |

Surfactants improve the solubility of Compound 1 . However, polysorbate 80 and polyoxyethylene (10) octylphenyl ether, which improved the solubility of Compound 1 to the same or greater extent than sodium lauryl sulfate, did not improve the disintegration of Compound 1.

Accordingly, it was suggested that improvement of solubility by surfactants does not improve the disintegration properties.
3 . Confirmation of the Dissolution Properties of Compound 1

The dissolution properties of the disintegrable formulations obtained as above were examined.

As shown in Table 4, capsules containing 1 mg, 5 mg, 10 mg, and 20 mg of Compound 1, respectively (hereinafter called "1 mg formulation", "20 mg formulation", and the like) were manufactured, and examined by a dissolution test. The ingredients were immediately released from the 1 mg, 5 mg and 10 mg formulations without problems, but the 20 mg formulation showed delayed dissolution.

This is presumably because, although the capsules are disintegrable, the particles of Compound 1 in the 20 mg formulation as dispersed in the test solution are larger than those in the 1 mg, 5 mg, and 10 mg formulations. Specifically, this is because the bonds between the particles in the 20 mg formulation cannot be sufficiently broken due to the high concentration of Compound 1.

Dissolution of the 20 mg formulation was improved by further extragranularly adding microcrystalline cellulose, an excipient, to prevent bonding between the drug substance particles.

(Manufacture of Formulations)

Examples 2 to 4 and Example 6

The ingredients listed in Table 4 (excluding magnesium stearate) were put in a high shear granulator and premixed. To this mixture was added 22% by weight (relative to the mixture) of purified water. The mixture was stirred, granulated, and then vacuum dried to provide a dry powder. The dry powder was subjected to particle size granulation by a sieving machine, and the size-granulated powder was mixed with magnesium stearate in the mixer to provide a compounded powder. The compounded powder was filled into a capsule shell to manufacture a capsule.

Example 5

The ingredients listed in Table 4 (excluding microcrystalline cellulose (extragranular) and magnesium stearate) were put in a high shear granulator and premixed. To this mixture was added 23% by weight (relative to the mixture) of purified water. The mixture was stirred, granulated, and then vacuum dried to provide a dry powder. The dry powder was subjected to particle size granulation by a sieving machine, and the size-granulated powder was mixed with microcrystalline cellulose (extragranular) and magnesium stearate in the mixer to provide a compounded powder. The compounded powder was filled into a capsule shell to manufacture a capsule.

TABLE 4

| Content per capsule (mg) | | | | | |
|---|---|---|---|---|---|
| | Example 2 | Example 3 | Example 4 | Example 5 | Example 6 |
| Compound 1 malate bulk drug (as free form) | 1.4 (1.0) | 6.9 (5.0) | 13.8 (10.0) | 27.5 (20.0) | 27.5 (20.0) |
| Lactose hydrate | 137.6 | 132.1 | 125.2 | 111.5 | 111.5 |
| Crystalline cellulose | 30.0 | 30.0 | 30.0 | 30.0 | 30.0 |
| Croscarmellose Na | 10.0 | 10.0 | 10.0 | 10.0 | 10.0 |
| Hydroxypropylcellulose | 10.0 | 10.0 | 10.0 | 10.0 | 10.0 |
| Sodium lauryl sulfate | 10.0 | 10.0 | 10.0 | 10.0 | 10.0 |
| Crystalline cellulose (extragranular) | | | | 49.8 | |
| Magnesium stearate | 1.0 | 1.0 | 1.0 | 1.2 | 1.0 |
| Total | 200 | 200 | 200 | 250 | 200 |

(Evaluation of Formulations)

Examples 2 to 5 and Example 6 were tested by the paddle dissolution test method according to the Japanese Pharmacopoeia at 75 rpm using 900 mL of Dissolution Test Solution 1 of the Japanese Pharmacopoeia containing 1% polyoxyethylene (10) octylphenyl ether as the test solution. The dissolution profiles are shown in FIGS. 1 and 2.

Figure 2:
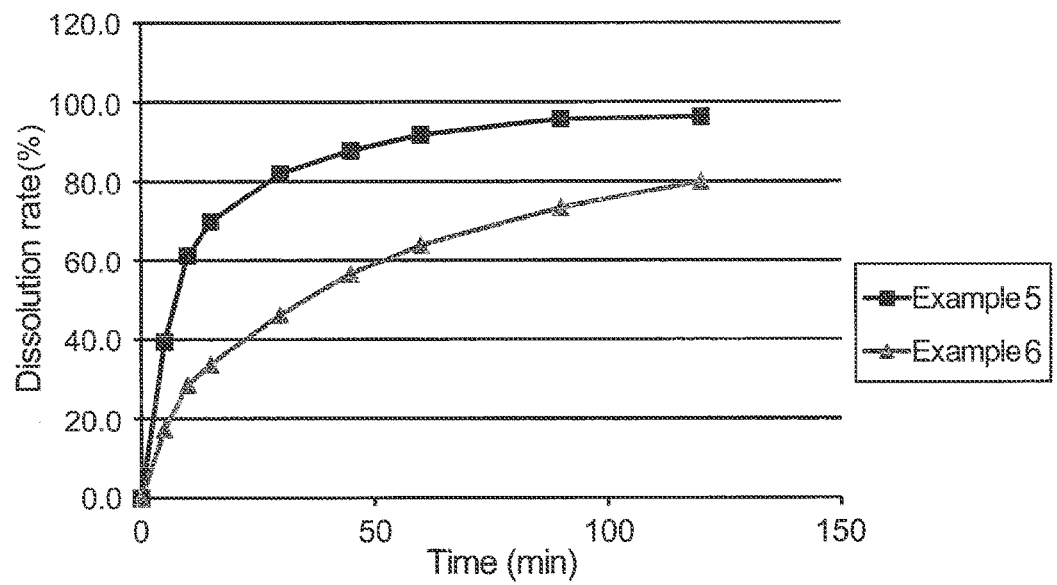
FIG. 2 is a graph showing dissolution profiles for capsules containing 20.0 mg of Compound 1 (in terms of free form) in the presence and absence of crystalline cellulose, respectively (Examples 5 and 6).

FIG. 1 shows that Examples 2, 3, and 4 are encapsulated formulations containing 1 mg, 5 mg, and 10 mg of Compound 1, respectively, and are immediate release formulations. FIG. 2 shows that a 20 mg capsule formulation manufactured in the same manner tends to show decreased dissolution as with Example 6. An immediate release formulation can be prepared by extragranularly adding microcrystalline cellulose as in Example 5.

4. Dissolution Properties and Tableting when the Concentration of Compound 1 is High Capsules containing a dose of 20 mg or more of a drug substance are usually made by increasing the concentration of the drug substance or increasing the capsule size. However, as shown in Examples 5 and 6, it is difficult to increase the drug substance concentration. Moreover, large capsules are hard to swallow and thus cannot easily be accepted in the market. Therefore, other dosage forms are preferred when developing formulations containing 20 mg or more of a drug substance.

Poor dissolution of high dose capsules is due to poor disintegration of the capsules. Specifically, it is because disintegrants do not work effectively and cannot disintegrate the formulations sufficiently. Typically, disintegrants are classified into wicking disintegrants (causing water infiltration to break the bond between particles) and swelling disintegrants (absorbing water and swelling to break the bond between particles). Since the poor disintegration of Compound 1 is caused by particles adsorbed to each other by water, swelling disintegrants were considered to be highly effective.

However, swelling disintegrants must sufficiently swell to break the bonds between particles. Super disintegrants such as croscarmellose sodium are disintegrants having a swelling rate of more than 200%. The research by the present inventors revealed that it is difficult even for such disintegrants to disintegrate commonly used capsules containing 20 mg or more of Compound 1 per capsule.

The present inventors elucidated that this is due to voids created when powder is filled into a capsule shell. Specifically, this is because swollen disintegrants escape into the voids, allowing the force for breaking the bonds between particles to be spread out.

Accordingly, tableting was attempted to eliminate such voids. As shown below, the use of disintegrants having a high swelling rate and void-eliminating formulation provided excellent disintegration and dissolution properties even for high dose formulations.

(Manufacture of Formulations)

Examples 7 and 8 and Reference Examples 1 and 2

The ingredients listed in Table 5 (excluding magnesium stearate) were put in a mortar and premixed. To this mixture was added 20% by weight (relative to the mixture) of purified water. The mixture was stirred, granulated, and then dried to provide a dry powder. The dry powder was subjected to particle size granulation by a sieve, and the size-granulated powder was mixed with magnesium stearate in the mortar to provide a compounded powder. The compounded powder was tableted to prepare a tablet as Example 7 or 8, and the compounded powder was filled into a capsule shell to prepare a capsule as Reference Example 1 or 2.

TABLE 5

| Content per tablet or capsule (mg) | | |
|---|---|---|
| | Example 7 (tablet) Reference Example 1 (capsule) | Example 8 (tablet) Reference Example 2 (capsule) |
| Compound 1 malate bulk drug (as free form) | 55.0 (40 mg) | 110.2 (80 mg) |
| Lactose hydrate | 74.0 | 18.8 |
| Crystalline cellulose | 30.0 | 10.0 |
| Croscarmellose Na | 10.0 | 10.0 |
| Hydroxypropylcellulose | 10.0 | 10.0 |
| Sodium lauryl sulfate | 20.0 | 40.0 |
| Magnesium stearate | 1.0 | 1.0 |
| Total | 200 | 200 |

(Evaluation of Formulations)

Disintegration properties of Examples 7 and 8 and Reference Examples 1 and 2 in a. dissolution tester were visually observed using Dissolution Test Solution 1 of the Japanese Pharmacopoeia. The results are shown in Table 6.

TABLE 6

|  | Reference Example 7 | Example 1 | Reference Example 8 | Example 2 |
|---|---|---|---|---|
| Disintegration properties in Dissolution Test Solution 1 of the Japanese Pharmacopoeia | ○ | × | ○ | × | o: disintegrated within 60 minutes
x: not disintegrated within 60 minutes

Further, as disintegrable formulations were provided by tableting as described above, tablets were manufactured by an instrument and their dissolution properties were examined as shown in Examples 9 and 10 below. For convenience, the amount of the compounded powder was increased by 1.25-fold to manufacture tablets containing 50 mg and 100 mg of the principal agent, respectively.

(Manufacture of Formulations)

Examples 9 and 10

The ingredients listed in Table 7 (excluding magnesium stearate) were put in a high sheargranulator and premixed. To this mixture was added 20% by weight (relative to the mixture) of purified water for Example 9, or 18% by weight of purified water for Example 10. The mixture was stirred, granulated, and then vacuum dried to provide a dry powder. The dry powder was subjected to particle size granulation by a sieving machine, and the size-granulated powder was mixed with magnesium stearate in the mixer to provide a compounded powder. The compounded powder was tableted to prepare a tablet as Example 9 or 10.

TABLE 7

| Content per tablet (mg) | | |
|---|---|---|
|  | Example 9 (tablet) | Example 10 (tablet) |
| Compound 1 malate bulk drug (as free form) | 68.8 (50 mg) | 137.6 (100 mg) |
| Lactose hydrate | 92.4 | 23.6 |
| Crystalline cellulose | 37.5 | 12.5 |
| Croscarmellose Na | 12.5 | 12.5 |
| Hydroxypropylcellulose | 12.5 | 12.5 |
| Sodium lauryl sulfate | 25.0 | 50.0 |
| Magnesium stearate | 1.3 | 1.3 |
| Total | 250 | 250 |

(Evaluation of Formulations)

Figure 3:
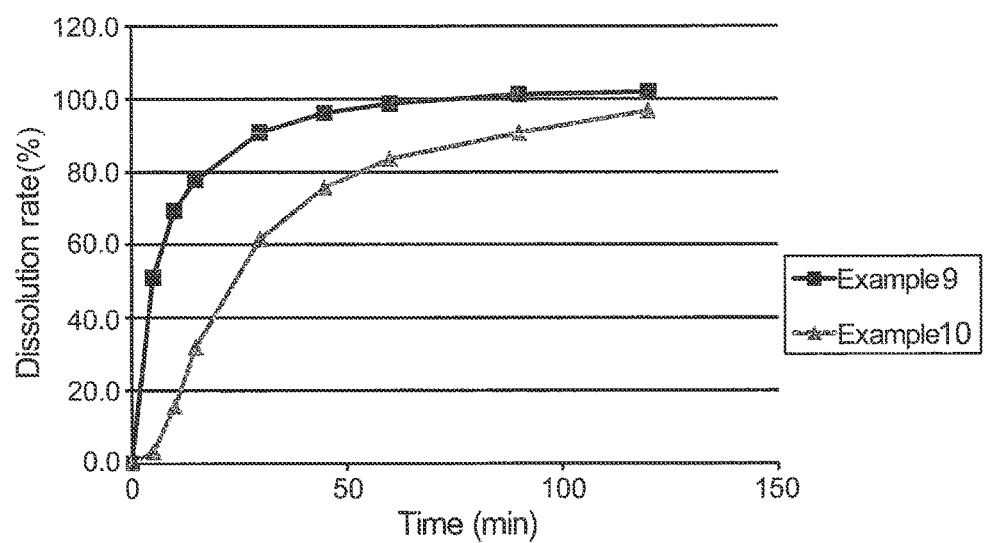
FIG. 3 is a graph showing dissolution profiles for tablets containing 50.0 mg and 100.0 mg of Compound I (in terms of free form), respectively (Examples 9 and 10).

Examples 9 and 10 were tested by the paddle dissolution test method according to the Japanese Pharmacopoeia at 75 rpm using 900 mL of Dissolution Test Solution 1 of the Japanese Pharmacopoeia containing 1% polyoxyethylene (10) octylphenyl ether as the test solution. The dissolution profiles are shown in FIG. 3.

5. Evaluation of Combining SLS and Super Disintegrants for Compound 1

The following Comparative Examples also suggest that the combination of SLS with a super disintegrant is extremely suitable.

Examples 7, 8, 9, and 10 revealed that, when SLS is used, even high dose formulations containing 50 mg to 100 mg of Compound 1 become disintegrable by being tableted. On the other hand, as shown following Comparative Examples 6 and 7, formulations tableted using other surfactants instead of SLS were not disintegrated within 60 minutes even in the presence of a super disintegrant and even when the content of Compound 1 was as low as 20 mg. This shows that not only the addition of SLS but also the combination of SLS and a super disintegrant is advantageous for pharmaceutical formulations containing Compound 1.

(Manufacture of Formulations)

The ingredients listed in Table 8 (excluding magnesium stearate) were put in a mortar and premixed. To this mixture was added 20% by weight (relative to the mixture) of purified water. The mixture was stirred, granulated, and then dried to provide a dry powder. The dry powder was subjected to particle size granulation by a sieve, and the size-granulated powder was mixed with magnesium stearate in the mortar to provide a compounded powder.

The compounded powder was tableted to manufacture a tablet.

TABLE 8

| Content per tablet (mg) | | |
|---|---|---|
|  | Comparative Example 6 | Comparative Example 7 |
| Compound 1 malat ebulk drug (as free form) | 27.5 (20) | 27.5 (20) |
| Lactose hydrate | 111.5 | 111.5 |
| Crystalline cellulose | 30.0 | 30.0 |
| Croscarmellose Na | 10.0 | 10.0 |
| Hydroxypropylcellulose | 10.0 | 10.0 |
| Polysorbate 80 | 10.0 |  |
| Polyoxyethylene (10) octylphenyl ether |  | 10.0 |
| Magnesium stearate | 1.0 | 1.0 |
| Total | 200 | 200 |

(Evaluation of Formulations)

Disintegration properties of Comparative Examples 6 and 7 in a dissolution tester were visual observed using Dissolution Test Solution 1 of the Japanese Pharmacopoeia. The results are shown in Table 9.

TABLE 9

|  | Comparative Example 6 | Comparative Example 7 |
|---|---|---|
| Disintegration properties in Dissolution Test Solution 1 of the Japanese Pharmacopoeia | × | × | o: disintegrated within 60 minutes
x: not disintegrated within 60 minutes

6. Manufacturing Method

In formulating poorly soluble Compound 1, improvement of the dissolution properties was attempted by optimizing the granulation method, but the formulation was not disintegrated when common granulation was performed. As described above, addition of SLS improved the disintegration properties of the formulation.

(Manufacture of Formulations)

Examples 11 to 14

The ingredients listed in Table 10 (excluding magnesium stearate) were put in a high shear granulator and premixed. To this mixture was added purified water at a weight ratio shown in Table 10 (relative to the mixture). The mixture was stirred, granulated, and then vacuum dried to provide a dry powder. The dry powder was subjected to particle size granulation by a sieving machine, and the size-granulated powder was mixed with magnesium stearate in the mixer to provide a compounded powder. The compounded powder was tableted to prepare a tablet.

TABLE 10

|  | Example 11 | Example 12 | Example 13 | Example 14 |
|---|---|---|---|---|
| Compound 1 malate bulk drug (as free form) | 68.8 (50 mg) | ← | ← | ← |
| Lactose hydrate | 92.4 | ← | ← | ← |
| Crystalline cellulose | 37.5 | ← | ← | ← |
| Croscarmellose Na | 12.5 | ← | ← | ← |
| Hydroxypropylcellulose | 12.5 | ← | ← | ← |
| Sodium lauryl sulfate | 25.0 | ← | ← | ← |
| Magnesium stearate | 1.3 | ← | ← | ← |
| Total | 250 | ← | ← | ← |
| Purified water | 10% | 25% | 30% | 40% |

(Evaluation of Formulations)

Disintegration properties of Examples 9 and 11 to 14 in a dissolution tester were visually observed using Dissolution Test Solution 1 of the Japanese Pharmacopoeia. The results are shown in Table 11.

TABLE 11

| seven minutes, | Amount of purified water | Disintegration properties in Dissolution Test Solution 1 of the Japanese Pharmacopoeia |
|---|---|---|
| Example 11 | 10% | Started disintegration within 30 seconds, disintegrated within 10 minutes |
| Example 9 | 20% | Started disintegration within 30 seconds, disintegrated within 10 minutes |
| Example 12 | 25% | Started disintegration in about one minute, disintegrated within 10 minutes |
| Example 13 | 30% | Started disintegration in about seven minutes, not disintegrated within 30 minutes |
| Example 14 | 40% | Started disintegration in about 10 minutes, not disintegrated within 30 minutes |

As is clear from the above results, the preferred amount of purified water is 25% by weight or less relative to the mixture.

INDUSTRIAL APPLICABILITY

The pharmaceutical formulations according to the present invention are extremely useful as pharmaceutical formulations, because they comprise an alkyl sulfate salt and therefore have excellent dissolution properties without causing gelation of the compound particles.

The invention claimed is:

1. A pharmaceutical formulation comprising
an alkyl sulfate salt; and
a compound represented by general formula (I) below, or a tautomer of the compound, or a pharmaceutically acceptable salt of the compound or tautomer:

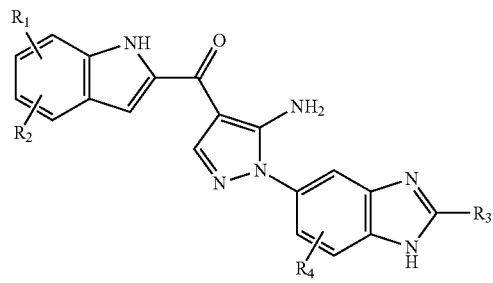

wherein $R_1$ to $R_4$ each independently represents the group listed below:
$R_1$ represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{3-7}$ cycloalkyl, $C_{6-10}$ aryl-$C_{1-4}$ alkyl, —$OR_5$, —$NR_6R_7$, —$(CR_8R_9)_nZ_1$, —$C(O)NR_{12}R_{13}$, —$SR_{14}$, —$SOR_{15}$, —$SO_2R_{16}$, —$NR_{17}SO_2R_{18}$, COOH, $C_{6-10}$ aryl optionally substituted with one or more groups independently selected from Group P, 5- to 10-membered heteroaryl or 3- to 10-membered heterocyclyl optionally substituted with one or more groups independently selected from Group Q, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$;

$R_2$ represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{3-7}$ cycloalkyl, $C_{6-10}$ aryl-$C_{1-4}$ alkyl, —$OR_5$, —$NR_6R_7$, —$(CR_8R_9)_nZ_1$, —$C(O)NR_{12}R_{13}$, —$SR_{14}$, —$SOR_{15}$, —$SO_2R_{16}$, —$NR_{17}SO_2R_{18}$, COOH, $C_{6-10}$ aryl optionally substituted with one or more groups independently selected from Group P, 5- to 10-membered heteroaryl or 3- to 10-membered heterocyclyl optionally substituted with one or more groups independently selected from Group Q, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$; or $R_1$ and $R_2$, together with the atoms to which they are bound, form 3- to 10-membered heterocyclyl or 5- to 10-membered heteroaryl, wherein the heterocyclyl or the heteroaryl is optionally substituted with halogen;

$R_3$ represents hydrogen, $C_{1-5}$ alkyl, $C_{6-10}$ aryl-$C_{1-6}$ alkyl, or $C_{1-4}$ haloalkyl;

$R_4$ represents hydrogen, halogen, $C_{1-3}$ alkyl, $C_{1-3}$ perfluoroalkyl, cyano, methanesulfonyl, hydroxyl, alkoxy, or amino;

$R_5$ represents $C_{1-5}$ alkyl, $C_{3-7}$ cycloalkyl, $C_{3-7}$ cycloalkyl-$C_{1-3}$ alkyl, $C_{2-6}$ alkenyl, $C_{2-6}$ alkynyl, $C_{1-4}$ haloalkyl, $C_{1-3}$ alkoxy-$C_{1-4}$ alkyl, $C_{1-3}$ alkoxy-$C_{1-4}$ alkoxy-$C_{1-4}$ alkyl, $C_{1-4}$ aminoalkyl, $C_{1-4}$ alkylamino-$C_{1-4}$ alkyl, di($C_{1-4}$ alkyl)amino-$C_{1-4}$ alkyl, $C_{6-10}$ aryl, $C_{6-10}$ aryl-$C_{1-3}$ alkyl, 3- to 10-membered heterocyclyl-$C_{1-3}$ alkyl optionally substituted with one or more groups independently selected from Group Q, 3- to 10-membered heterocyclyl, 5- to 10-membered heteroaryl, 5- to 10-membered heteroaryl-$C_{1-3}$ alkyl, $C_{1-6}$ monohydroxyalkyl, $C_{1-6}$ dihydroxyalkyl, or $C_{1-6}$ trihydroxyalkyl;

$R_6$ and $R_7$ are the same or different, and each represents hydrogen, $C_{1-4}$ alkyl, $C_{2-6}$ alkenyl, $C_{2-6}$ alkynyl, $C_{1-4}$ haloalkyl, $C_{1-3}$ alkoxy-$C_{1-4}$ alkyl, $C_{6-10}$ aryl-$C_{1-3}$ alkyl, 3- to 10-membered heterocyclyl-$C_{1-3}$ alkyl, 5- to 10-membered heteroaryl-$C_{1-3}$ alkyl, $C_{1-6}$ monohydroxyalkyl, $C_{1-6}$ dihydroxyalkyl, $C_{1-6}$ trihydroxyalkyl, 3- to 10-membered heterocyclyl, $C_{1-4}$ aminoalkyl, $C_{1-4}$ alkylamino-$C_{1-4}$ alkyl, di($C_{1-4}$ alkyl)amino-$C_{1-4}$ alkyl, or cyano($C_{1-3}$ alkyl); or $R_6$ and $R_7$, together with the nitrogen atom to which they are bound, form 3- to 10-membered heterocyclyl or 5- to 10-membered heteroaryl;

n represents 1 to 3;

$R_8$ and $R_9$ are the same or different, and each represents hydrogen, $C_{1-4}$ alkyl, or halogen; or $R_8$ and $R_9$, together with the carbon atom to which they are bound, form an alicyclic ring;

$Z_1$ represents hydrogen, $NR_{10}R_{11}$, —OH, or 3- to 10-membered heterocyclyl or 5- to 10-membered heteroaryl optionally substituted with one or more groups independently selected from Group Q;

$R_{10}$ and $R_{11}$ are the same or different, and each represents $C_{1-4}$ alkyl, $C_{2-6}$ alkenyl, $C_{2-6}$ alkynyl, $C_{1-4}$ haloalkyl, $C_{1-3}$ alkoxy-$C_{1-4}$ alkyl, cyano($C_{1-3}$ alkyl), or $C_{1-3}$ alkylsulfonyl-$C_{1-4}$ alkyl; or $R_{10}$ and $R_{11}$, together with the nitrogen atom to which they are bound, form 3- to 10-membered heterocyclyl or 5- to 10-membered heteroaryl;

$R_{12}$ and $R_{13}$ are the same or different, and each represents hydrogen, $C_{1-4}$ alkyl, $C_{2-6}$ alkenyl, $C_{2-6}$ alkynyl, $C_{1-4}$ haloalkyl, $C_{1-3}$ alkoxy-$C_{1-4}$ alkyl, $C_{6-10}$ aryl, 5- to 10-membered heteroaryl, 3- to 10-membered heterocyclyl, $C_{6-10}$ aryl-$C_{1-4}$ alkyl, 3- to 10-membered heterocyclyl-$C_{1-3}$ alkyl, 5to 10-membered heteroaryl-$C_{1-3}$ alkyl, cyano($C_{1-3}$ alkyl), $C_{1-3}$ alkylsulfonyl-$C_{1-4}$ alkyl, a 3- to 10-membered alicyclic ring, 5- to 10-membered heteroaryl, or 3- to 10-membered heterocyclyl; or $R_{12}$ and $R_{13}$, together with the nitrogen atom to which they are bound, form 3- to 10-membered heterocyclyl or 5- to 10-membered heteroaryl optionally substituted with one or more groups independently selected from Group Q;

$R_{14}$ represents $C_{1-4}$ alkyl, $C_{2-6}$ alkenyl, $C_{2-6}$ alkynyl, $C_{1-4}$ haloalkyl, $C_{6-10}$ aryl optionally substituted with one or more groups independently selected from Group P, or 5- to 10-membered heteroaryl or 3- to 10-membered heterocyclyl optionally substituted with one or more groups independently selected from Group Q;

$R_{15}$ represents $C_{1-4}$ alkyl, $C_{2-6}$ alkenyl, $C_{2-6}$ alkynyl, $C_{1-4}$ haloalkyl, $C_{6-10}$ aryl optionally substituted with one or more groups independently selected from Group P, or 5- to 10-membered heteroaryl or 3- to 10-membered heterocyclyl optionally substituted with one or more groups independently selected from Group Q;

$R_{16}$ represents $C_{1-4}$ alkyl, $C_{2-6}$ alkenyl, $C_{2-6}$ alkynyl, $C_{1-4}$ haloalkyl, $C_{6-10}$ aryl optionally substituted with one or more groups independently selected from Group P, or 5- to 10-membered heteroaryl or 3- to 10-membered heterocyclyl optionally substituted with one or more groups independently selected from Group Q;

$R_{17}$ represents hydrogen or $C_{1-4}$ alkyl;

$R_{18}$ represents $C_{1-4}$ alkyl, $C_{2-6}$ alkenyl, $C_{2-6}$ alkynyl, $C_{1-4}$ haloalkyl, $C_{6-10}$ aryl optionally substituted with one or more groups independently selected from Group P, or 5- to 10-membered heteroaryl or 3- to 10-membered heterocyclyl optionally substituted with one or more groups independently selected from Group Q;

$R_{19}$ represents hydrogen, $C_{1-4}$ alkyl, $C_{3-7}$ cycloalkyl, $C_{1-4}$ haloalkyl, $C_{6-10}$ aryl, or 5- to 10-membered heteroaryl or 3- to 10-membered heterocyclyl optionally substituted with one or more groups independently selected from Group Q;

$R_{20}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{21}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{22}$ represents hydrogen, $C_{1-4}$ alkyl, or $C_{1-4}$ haloalkyl;

$R_{23}$ represents hydrogen, $C_{1-4}$ alkyl, $C_{3-7}$ cycloalkyl, $C_{1-4}$ haloalkyl, $C_{6-10}$ aryl, 5- to 10membered heteroaryl, or 3- to 10-membered heterocyclyl;

$R_{24}$ represents hydrogen, $C_{1-4}$ alkyl, or $C_{1-4}$ haloalkyl;

$R_{25}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{26}$ and $R_{27}$ are the same or different, and each represents hydrogen, $C_{1-4}$ alkyl, $C_{2-6}$ alkenyl, $C_{2-6}$ alkynyl, $C_{1-4}$ haloalkyl, $C_{1-3}$ alkoxyl-$C_{1-4}$ alkyl, $C_{6-10}$ aryl, 5- to 10-membered heteroaryl, 3- to 10-membered heterocyclyl, $C_{6-10}$ aryl-$C_{1-4}$ alkyl, 3- to 10-membered heterocyclyl-$C_{1-3}$ alkyl, 5- to 10-membered heteroaryl-$C_{1-3}$ alkyl, cyano($C_{1-3}$ alkyl), $C_{1-3}$ alkylsulfonyl-$C_{1-4}$ alkyl, or a 3- to 10-membered alicyclic ring; or $R_{26}$ and $R_{27}$, together with the nitrogen atom to which they are bound, form 3- to 10-membered heterocyclyl or 5- to 10-membered heteroaryl;

$R_{28}$ and $R_{29}$ are the same or different, and each represents hydrogen, $C_{1-4}$ alkyl, $C_{2-6}$ alkenyl, $C_{2-6}$ alkynyl, $C_{1-4}$ haloalkyl, $C_{1-3}$ alkoxyl-$C_{1-4}$ alkyl, $C_{6-10}$ aryl, 5- to 10-membered heteroaryl, 3- to 10-membered heterocyclyl, $C_{6-10}$ aryl-$C_{1-4}$ alkyl, 3- to 10-membered heterocyclyl-$C_{1-3}$ alkyl, 5- to 10-membered heteroaryl-$C_{1-3}$ alkyl, cyano($C_{1-3}$ alkyl), $C_{1-3}$ alkylsulfonyl-$C_{1-4}$ alkyl, or a 3- to 10-membered alicyclic ring; or $R_{28}$ and $R_{29}$, together with the nitrogen atom to which they are bound, form 3- to 10-membered heterocyclyl or 5- to 10-membered heteroaryl;

$R_{30}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{31}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{32}$ represents $C_{1-4}$ alkyl or $C_{6-10}$ aryl;

Group P is halogen, $C_{1-4}$ alkyl, $C_{1-4}$ haloalkyl, —OH, $_{1-3}$ alkoxy, $C_{1-3}$ haloalkoxy, 3- to 10-membered heterocyclylamino, —$SO_2R_{16}$, —CN, —$NO_2$, or 3- to 10-membered heterocyclyl; and Group Q is halogen, $C_{1-4}$ alkyl, $C_{1-4}$ haloalkyl, —OH, $C_{1-3}$ alkoxy, $C_{1-6}$ monohydroxyalkyl, $C_{1-6}$ dihydroxyalkyl, or $C_{1-6}$ trihydroxyalkyl, 3- to 10-membered heterocyclylamine, —$SO_2R_{16}$, —CN, —$NO_2$, $C_{3-7}$ cycloalkyl, —$COR_{19}$, or 3- to 10-membered heterocyclyl optionally substituted with $C_{1-4}$ alkyl.

2. The pharmaceutical formulation of claim 1, wherein $R_3$ is $C_{1-4}$ alkyl.

3. The pharmaceutical formulation of claim 1, wherein $R_4$ is hydrogen.

4. The pharmaceutical formulation of claim 1, wherein $R_1$ and $R_2$ are hydrogen.

5. A pharmaceutical formulation comprising:
an alkyl sulfate salt; and
compound 1 represented by:

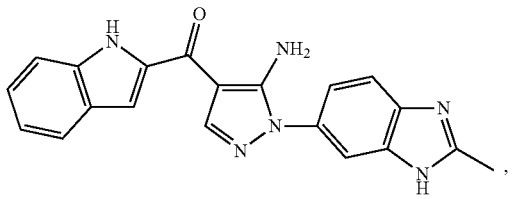 [SMILES: Cc1nc2ccc(-n3ncc(C(=O)c4cc5ccccc5[nH]4)c3N)cc2[nH]1]

or a tautomer of compound 1, or a pharmaceutically acceptable salt of compound 1 or the tautomer of compound 1.

6. The pharmaceutical formulation of claim 1, wherein the alkyl sulfate salt is a $C_{10-14}$ alkyl sulfate salt.

7. The pharmaceutical formulation of claim 1, wherein the alkyl sulfate salt is a lauryl sulfate salt.

8. The pharmaceutical formulation of claim 1, wherein the pharmaceutical formulation is a solid formulation.

9. The pharmaceutical formulation of claim 8, wherein the solid formulation is in the form of a capsule, tablet, powder, granule, or dry syrup.

10. The pharmaceutical formulation of claim 1, wherein the compound represented by general formula (I), or the tautomer, or the pharmaceutically acceptable salt of the compound or tautomer is in the form of particles having an average particle size of 10 μm or less.

11. The pharmaceutical formulation of any one of claim 1, further comprising a disintegrant.

12. The pharmaceutical formulation of claim 11, wherein the disintegrant is a super disintegrant.

13. The pharmaceutical formulation of claim 11, wherein the disintegrant is at least one selected from the group consisting of croscarmellose sodium, carmellose calcium, crospovidone, sodium carboxymethyl starch, low-substituted hydroxypropylcellulose, corn starch, and soybean polysaccharide.

14. The pharmaceutical formulation of claim 1, wherein the pharmaceutical formulation is in the form of a capsule comprising a shell, and wherein 10% by weight or less of the pharmaceutical formulation, excluding the weight of the capsule shell, is the compound represented by formula (I), or the tautomer, or the pharmaceutically acceptable salt of the compound or tautomer, in terms of free form.

15. The pharmaceutical formulation of claim 14, wherein the capsule comprises 20 mg or more, in terms of free form, of the compound represented by formula (I), or the tautomer, or the pharmaceutically acceptable salt of the compound or tautomer.

16. The pharmaceutical formulation of claim 1, wherein the pharmaceutical formulation is in the form of a capsule and further comprises extragranular crystalline cellulose.

17. The pharmaceutical formulation of claim 1, wherein the pharmaceutical formulation is in the form of a tablet.

18. The pharmaceutical formulation of claim 17, wherein the pharmaceutical formulation comprises compound 1 represented by:

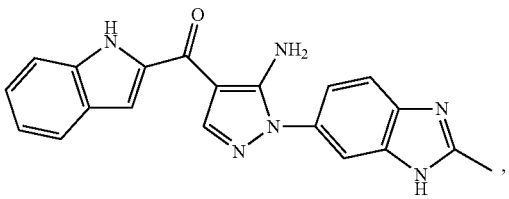 [SMILES: Cc1nc2ccc(-n3ncc(C(=O)c4cc5ccccc5[nH]4)c3N)cc2[nH]1]

or a tautomer of compound 1, or a pharmaceutically acceptable salt of compound 1 or of a tautomer of compound 1; sodium lauryl sulfate; and a super disintegrant.

19. The pharmaceutical formulation of claim 17, wherein the tablet comprises 1% to 50% by weight of the compound represented by formula (I), or the tautomer, or the pharmaceutically acceptable salt of the compound or tautomer, in terms of free form.

20. The pharmaceutical formulation of claim 17, wherein the ratio by weight between (a) the compound represented by formula (I), or the tautomer, or the pharmaceutically acceptable salt of the compound or tautomer, in terms of free form, and (b) the alkyl sulfate salt is 1:10 to 8:1.

21. The pharmaceutical formulation of claim 17, wherein the tablet's content by weight of the compound represented by formula (I), or the tautomer, or the pharmaceutically acceptable salt of the compound or tautomer, in terms of free form, is 1 mg to 500 mg.

22. A method for manufacturing a solid composition comprising the pharmaceutical formulation of claim 1, the method comprising:
providing a mixture comprising an alkyl sulfate salt and the compound represented by general formula (I), or the tautomer, or the pharmaceutically acceptable salt of the compound or tautomer;
granulating the mixture in the absence of water, or in the presence of water in an amount that is 25% by weight or less of the total weight of the mixture; and
producing a dry powder from the granulated mixture.

23. The manufacturing method of claim 22, further comprising:
subjecting the dry powder to particle size granulation to form a particle size-granulated powder;
mixing the particle size-granulated powder and an additive comprising magnesium stearate to form a compounded powder; and
tableting the compounded powder to produce a tablet.

24. The pharmaceutical formulation of claim 1, wherein the formulation is a solid formulation.

25. A method for treating cancer, comprising:
administering a pharmaceutically effective amount of the pharmaceutical formulation of claim 1 to a patient in need of treatment of cancer.

26. The method of claim 25, wherein the cancer is breast cancer, acute myeloid leukemia, pancreatic cancer, bladder cancer, prostatic cancer, esophageal cancer, angiogenesis, gastric cancer, endometrial cancer, ovarian cancer, brain tumor, colon cancer, multiple myeloma, hepatoma, lung cancer, or thyroid cancer.

27. The pharmaceutical formulation of claim 1, further comprising a lubricant.

28. The pharmaceutical formulation of claim 5, comprising a malate salt of compound 1.

29. The pharmaceutical formulation of claim 5, wherein the alkyl sulfate salt is a $C_{10-14}$ alkyl sulfate salt.

30. The pharmaceutical formulation of claim 5, wherein the alkyl sulfate salt is a lauryl sulfate salt.

31. The pharmaceutical formulation of claim 5, wherein the pharmaceutical formulation is a solid formulation.

32. The pharmaceutical formulation of claim 31, wherein the solid formulation is in the form of a capsule, tablet, powder, granule, or dry syrup.

33. The pharmaceutical formulation of claim 5, wherein the compound represented by general formula (I), or the tautomer, or the pharmaceutically acceptable salt of the compound or tautomer is in the form of particles having an average particle size of 10 μor less.

34. The pharmaceutical formulation of claim 5, further comprising a disintegrant.

35. The pharmaceutical formulation of claim 34, wherein the disintegrant is a super disintegrant.

36. The pharmaceutical formulation of claim 34, wherein the disintegrant is at least one selected from the group consisting of croscarmellose sodium, carmellose calcium, crospovidone, sodium carboxymethyl starch, low-substituted hydroxypropylcellulose, corn starch, and soybean polysaccharide.

37. The pharmaceutical formulation of claim 5, wherein the pharmaceutical formulation is in the form of a capsule comprising a shell, and wherein 10% by weight or less of the pharmaceutical formulation, excluding the weight of the capsule shell, is the compound represented by formula (I), or the tautomer, or the pharmaceutically acceptable salt of the compound or tautomer, in terms of free form.

38. The pharmaceutical formulation of claim 37, wherein the capsule comprises 20 mg or more, in terms of free form, of the compound represented by formula (I), or the tautomer, or the pharmaceutically acceptable salt of the compound or tautomer.

39. The pharmaceutical formulation of claim 1, wherein the pharmaceutical formulation is in the form of a capsule and further comprises extragranular crystalline cellulose.

40. The pharmaceutical formulation of claim 1, wherein the pharmaceutical formulation is in the form of a tablet.

41. The pharmaceutical formulation of claim 40, wherein the tablet comprises 1% to 50% by weight of the compound represented by formula (I), or the tautomer, or the pharmaceutically acceptable salt of the compound or tautomer, in terms of free form.

42. The pharmaceutical formulation of claim 40, wherein the ratio by weight between (a) the compound represented by formula (I), or the tautomer, or the pharmaceutically acceptable salt of the compound or tautomer, in terms of free form, and (b) the alkyl sulfate salt is 1:10 to 8:1.

43. The pharmaceutical formulation of claim 40, wherein the tablet's content by weight of the compound represented by formula (I), or the tautomer, or the pharmaceutically acceptable salt of the compound or tautomer, in terms of free form, is 1 mg to 500 mg.

44. The pharmaceutical formulation of claim 20, wherein the ratio by weight between (a) the compound represented by formula (I), or the tautomer, or the pharmaceutically acceptable salt of the compound or tautomer, in terms of free form, and (b) the alkyl sulfate salt is 1:2 to 5:1.

45. The pharmaceutical formulation of claim 20, wherein the ratio by weight between (a) the compound represented by formula (I), or the tautomer, or the pharmaceutically acceptable salt of the compound or tautomer, in terms of free form, and (b) the alkyl sulfate salt is 2:1.

46. The method of claim 25, wherein the cancer is breast cancer, acute myeloid leukemia, pancreatic cancer, bladder cancer, prostatic cancer, esophageal cancer, gastric cancer, endometrial cancer, ovarian cancer, brain tumor, colon cancer, multiple myeloma, hepatoma, lung cancer, or thyroid cancer.

* * * * *

UNITED STATES PATENT AND TRADEMARK OFFICE
CERTIFICATE OF CORRECTION

PATENT NO. : 9,814,776 B2  
APPLICATION NO. : 14/430273  
DATED : November 14, 2017  
INVENTOR(S) : Jun Nihira, Kensuke Okazaki and Shiho Yoshimura Page 1 of 1

It is certified that error appears in the above-identified patent and that said Letters Patent is hereby corrected as shown below:

In the Claims

Column 43, Line 30: In Claim 1, delete "5to" and insert -- 5- to --, therefor.

Column 44, Line 13 (approx.): In Claim 1, delete "10membered" and insert -- 10-membered --, therefor.

Column 44, Line 51: In Claim 1, delete "-OH, $_{1-3}$" and insert -- -OH, $C_{1-3}$ --, therefor.

Column 45, Line 35: In Claim 11, delete "any one of".

Column 47, Line 10: In Claim 33, delete "µor" and insert -- µm or --, therefor.

Signed and Sealed this  
Thirtieth Day of January, 2018

Joseph Matal  
*Performing the Functions and Duties of the*  
*Under Secretary of Commerce for Intellectual Property and*  
*Director of the United States Patent and Trademark Office*